United States Patent
Hickey et al.

(10) Patent No.: US 11,441,166 B2
(45) Date of Patent: Sep. 13, 2022

(54) REDOX ENZYME-EMBEDDED PYRENE-POLY(ETHYLENIMINE) HYDROGEL ELECTRODE FOR ELECTROSYNTHESIS

(71) Applicant: University of Utah Research Foundation, Salt Lake City, UT (US)

(72) Inventors: David P. Hickey, Salt Lake City, UT (US); Shelley D. Minteer, Bountiful, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 499 days.

(21) Appl. No.: 16/405,859

(22) Filed: May 7, 2019

(65) Prior Publication Data

US 2020/0024631 A1    Jan. 23, 2020

Related U.S. Application Data

(60) Provisional application No. 62/704,005, filed on May 7, 2018.

(51) Int. Cl.
  *C12Q 1/00*   (2006.01)
  *C12Q 1/26*   (2006.01)
  *C08J 3/075*  (2006.01)

(52) U.S. Cl.
  CPC .............. *C12Q 1/005* (2013.01); *C08J 3/075* (2013.01); *C12Q 1/26* (2013.01); *C08J 2379/02* (2013.01); *C12Y 110/03002* (2013.01)

(58) Field of Classification Search
  None
  See application file for complete search history.

(56) References Cited

U.S. PATENT DOCUMENTS

2012/0080326 A1 * 4/2012 Chatelier ............ G01N 27/3273
                                                    205/782

FOREIGN PATENT DOCUMENTS

WO    WO-2017212304 A1 * 12/2017 ......... G01N 33/5438

OTHER PUBLICATIONS

J. Raba, et al. "Glucose Oxidase as an Analytical Reagent", Critical reviews in Analytical chemistry, 25(1): p. 1-42, Sep. 1995.*
D.P. Hickey, et al., "Enzyme Cascade for Catalyzing Sucrose Oxidation in a Biofuel Cell", ACS Catalysis, 3(12): p. 2729-2737, Dec. 2013.*

* cited by examiner

*Primary Examiner* — J. Christopher Ball
(74) *Attorney, Agent, or Firm* — Todd Alder

(57) ABSTRACT

Devices, systems, and compositions of matter involving enzyme-mediated bioelectrocatalysis are disclosed and described. An enzyme electrode can include an electrode, a bioelectric material coupled to the electrode, the bioelectric material further including a water-permeable polymer matrix, a planar linker covalently coupled to the water-permeable polymer matrix and noncovalently coupled to the electrode, and electrochemically active oxidoreductase enzyme molecules functionally embedded in the water-permeable polymer matrix.

18 Claims, 11 Drawing Sheets

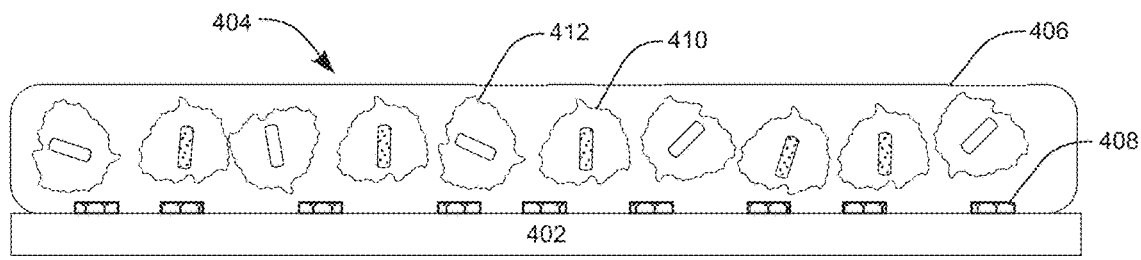
FIG. 4
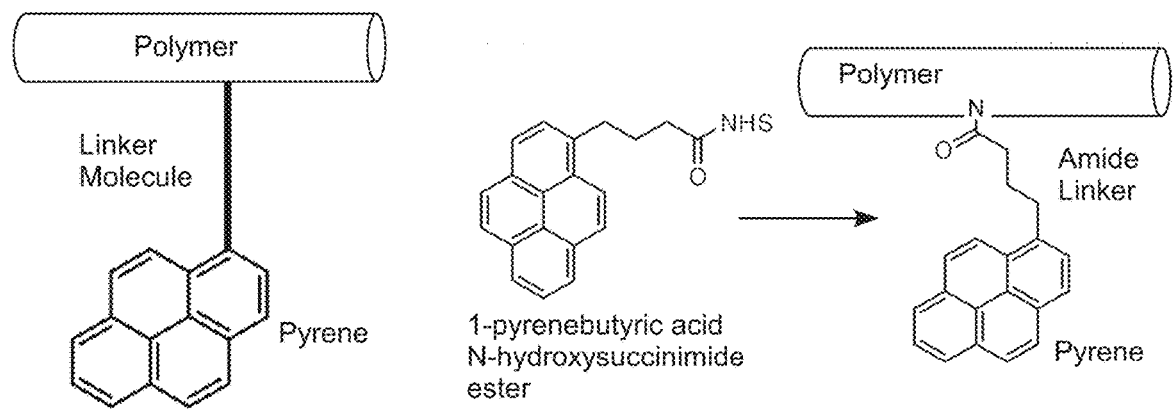
FIG. 5A
FIG. 5B
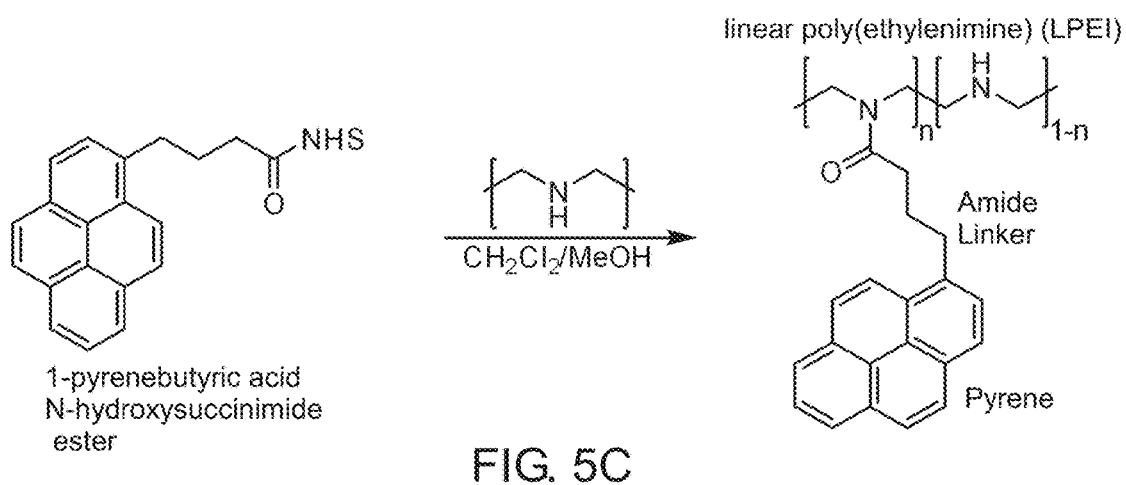
FIG. 5C

REDOX ENZYME-EMBEDDED PYRENE-POLY(ETHYLENIMINE) HYDROGEL ELECTRODE FOR ELECTROSYNTHESIS

CROSS-REFERENCE TO RELATED APPLICATIONS

This application claims the benefit of U.S. Provisional Patent Application No. 62/704,005, filed on May 7, 2018, which is incorporated herein by reference in its entirety.

GOVERNMENT INTEREST

This invention was made with government support under grant number DE-SC0017845 awarded by the Department of Energy. The government has certain rights in the invention.

BACKGROUND

Reduction-oxidation reactions (redox) are chemical reactions in which the oxidation states of atoms are changed. Such reactions involve both reduction and oxidation, which involve the transfer of electrons between chemical species. The chemical species from which the electron is stripped is said to have been oxidized, while the chemical species to which the electron is added is said to have been reduced.

Oxidoreductase enzymes are proteins that catalyze redox reactions in biological systems. Enzyme-based bioelectrocatalysis is the integration of the catalytic function of such oxidoreductase enzymes with an electrode reaction for the transfer of electrons therebetween. Such electrode reaction can be accomplished by mediated electron transfer (MET) or direct electron transfer (DET) between the active site of the enzyme and the electrode. MET reactions require a redox mediator to shuttle electrons between the active site of the enzyme and the electrode. DET reactions, on the other hand, can occur when the active sites of enzymes can be located close to the surface of the current collector to tunnel electrons between the enzyme and the current collector, thereby exhibiting electrocatalytic activity without the need for a redox mediator. The main drawback of DET-based designs, however, is their low current output efficiency, which is limited by the density of electroactive enzymes on the electrode surface. This limiting factor is determined by the molecular size of the enzyme and the enzyme orientation relative to the electrode surface. As the electron transfer rate between the enzyme and the electrode exponentially depends on the inverse of the electron transfer distance, most enzymes on an electrode surface will generally show no electrocatalytic activity without proper control of the orientation.

BRIEF DESCRIPTION OF THE DRAWINGS

FIG. 4 illustrates an enzyme electrode in accordance with an example embodiment;

FIG. 5A illustrates a generic pyrene-modified polymer in accordance with an example embodiment;

FIG. 5B illustrates a reaction to generate a generic pyrene-modified polymer in accordance with an example embodiment;

FIG. 5C illustrates a reaction to generate a pyrene-modified LPEI polymer in accordance with an example embodiment;

DESCRIPTION OF EMBODIMENTS

Figure 1:
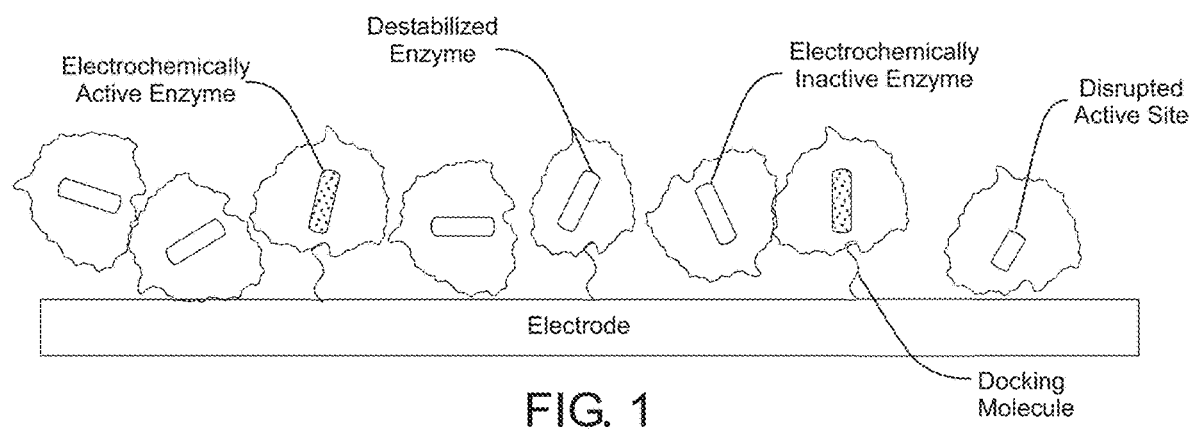
FIG. 1 illustrates a prior art biocatalytic electrode.

Although the following detailed description contains many specifics for the purpose of illustration, a person of ordinary skill in the art will appreciate that many variations and alterations to the following details can be made and are considered included herein. Accordingly, the following embodiments are set forth without any loss of generality to, and without imposing limitations upon, any claims set forth. It is also to be understood that the terminology used herein is for describing particular embodiments only and is not intended to be limiting. Unless defined otherwise, all technical and scientific terms used herein have the same meaning as commonly understood by one of ordinary skill in the art to which this disclosure belongs. Also, the same reference numerals in appearing in different drawings represent the same element. Numbers provided in flow charts and processes are provided for clarity in illustrating steps and operations and do not necessarily indicate a particular order or sequence.

Furthermore, the described features, structures, or characteristics can be combined in any suitable manner in one or more embodiments. In the following description, numerous specific details are provided, such as examples of layouts, distances, network examples, etc., to provide a thorough understanding of various embodiments. One skilled in the relevant art will recognize, however, that such detailed embodiments do not limit the overall concepts articulated herein but are merely representative thereof. One skilled in the relevant art will also recognize that the technology can be practiced without one or more of the specific details, or with other methods, components, layouts, etc. In other instances, well-known structures, materials, or operations may not be shown or described in detail to avoid obscuring aspects of the disclosure.

In this application, "comprises," "comprising," "containing" and "having" and the like can have the meaning ascribed to them in U.S. Patent law and can mean "includes," "including," and the like, and are generally interpreted to be open ended terms. The terms "consisting of" or "consists of" are closed terms, and include only the components, structures, steps, or the like specifically listed in conjunction with such terms, as well as that which is in accordance with U.S. Patent law. "Consisting essentially of" or "consists essentially of" have the meaning generally ascribed to them by U.S. Patent law. In particular, such terms are generally closed terms, with the exception of allowing inclusion of additional items, materials, components, steps, or elements, that do not materially affect the basic and novel characteristics or function of the item(s) used in connection therewith. For example, trace elements present in a composition, but not affecting the compositions nature or characteristics would be permissible if present under the "consisting essentially of" language, even though not expressly recited in a list of items following such terminology. When using an open-ended term in this written description, like "comprising" or "including," it is understood that direct support should be afforded also to "consisting essentially of" language as well as "consisting of" language as if stated explicitly and vice versa.

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result. For example, a composition that is "substantially free of" particles would either completely lack particles, or so nearly completely lack particles that the effect would be the same as if it completely lacked particles. In other words, a composition that is "substantially free of" an ingredient or element may still actually contain such item as long as there is no measurable effect thereof.

As used herein, the term "about" is used to provide flexibility to a given term, metric, value, range endpoint, or the like. The degree of flexibility for a particular variable can be readily determined by one skilled in the art. However, unless otherwise expressed, the term "about" generally provides flexibility of less than 1%, and in some cases less than 0.01%. It is to be understood that, even when the term "about" is used in the present specification in connection with a specific numerical value, support for the exact numerical value recited apart from the "about" terminology is also provided.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 1.5, 2, 2.3, 3, 3.8, 4, 4.6, 5, and 5.1 individually.

This same principle applies to ranges reciting only one numerical value as a minimum or a maximum. Furthermore, such an interpretation should apply regardless of the breadth of the range or the characteristics being described.

Reference throughout this specification to "an example" means that a particular feature, structure, or characteristic described in connection with the example is included in at least one embodiment. Thus, appearances of phrases including "an example" or "an embodiment" in various places throughout this specification are not necessarily all referring to the same example or embodiment.

The terms "first," "second," "third," "fourth," and the like in the description and in the claims, if any, are used for distinguishing between similar elements and not necessarily for describing a particular sequential or chronological order. It is to be understood that the terms so used are interchangeable under appropriate circumstances such that the embodiments described herein are, for example, capable of operation in sequences other than those illustrated or otherwise described herein. Similarly, if a method is described herein as comprising a series of steps, the order of such steps as presented herein is not necessarily the only order in which such steps may be performed, and certain of the stated steps may possibly be omitted and/or certain other steps not described herein may possibly be added to the method.

As used herein, comparative terms such as "increased," "decreased," "better," "worse," "higher," "lower," "enhanced," and the like refer to a property of a device, component, or activity that is measurably different from other devices, components, or activities in a surrounding or adjacent area, in a single device or in multiple comparable devices, in a group or class, in multiple groups or classes, or as compared to the known state of the art. For example, a data region that has an "increased" risk of corruption can refer to a region of a memory device which is more likely to have write errors to it than other regions in the same memory device. A number of factors can cause such increased risk, including location, fabrication process, number of program pulses applied to the region, etc.

Example Embodiments

An initial overview is provided below, and specific embodiments are then described in further detail. This initial summary is intended to aid readers in understanding the technology more quickly but is not intended to identify key or essential technological features, nor is it intended to limit the scope of the claimed subject matter.

Bioelectrocatalysis refers to reactions that are catalyzed by biologically active materials in association with electrically conductive electrodes. A given reaction tends to be very specific due to the correspondingly specific nature/functionality of the biologically active material to catalyze the reaction. The associated electrode functions, among other things, as an electron source or an electron sink for the biologically active material to continue catalyzing the reaction. The transfer of electrons to/from the electrode to the biologically active material, however, tends to be a limiting factor in such reactions that has limited the practical and commercial use of such bioelectrocatalytic processes.

Enzymes represent one class of biologically active material that can have a high utility for catalyzing bioelectrocatalytic reactions (i.e., enzymatic bioelectrocatalysis). In one general example of enzymatic bioelectrocatalysis, enzymes are associated with an electrode in a manner that allows electron transfer between the electrode and the enzymes. Such electron transfer allows the continued function of each enzyme over many catalyzed reactions. It is noted that the term "enzyme(s)" is used to describe biologically based catalytic materials throughout the present disclosure; this is, however, for convenience, and it is understood that any biologically active material can be substituted in such description for the term "enzyme(s)" unless the context clearly indicates otherwise. Nonlimiting examples of other biologically based catalytic materials can include eukaryotic cells, prokaryotic cells, cellular organelles, nucleic acid enzymes (i.e. deoxyribozymes), and the like.

Because the active sites of many enzymes are buried deep within an electrically insulated protein body, they are not electrochemically active. For such cases, electrons can be transferred between an electrode and the active site of an enzyme according to at least two general mechanisms; mediated electron transfer (MET) or direct electron transfer (DET), which can also be referred to as direct bioelectrocatalysis. According to MET techniques, an electrode is positioned in a liquid medium with the enzyme and a mediator compatible with the enzyme. The mediator functions to shuttle electrons from the electrode to the active site of the enzyme. Reaction designs using MET techniques, however, tend to have low reaction efficiencies and short functional lifetimes due, at least in part, to the long diffusion lengths between the active site of the enzyme and the electrode and instabilities of the mediators.

In DET techniques, on the other hand, enzyme active sites are positioned sufficiently close to the electrode surface to allow electrons to tunnel directly, without the need to involve a mediator. In some techniques, enzymes are coupled to the electrode surface via covalent bonding with a docking molecule. One primary drawback of prior DET designs, however, is their low efficiency due to the low density of electrochemically active enzymes on the electrode surface. One limiting factor is the orientation of enzymes on the electrode surface, as the electron transfer rate therebetween is inversely dependent on the electron transfer distance. So, enzymes oriented such that their active sites are not sufficiently close to the electrode surface will be electrocatalytically inactive due to the long electron transfer distance. Another limiting factor may be due to the immobilization of the enzyme to the electrode surface, such as by covalent bonding with a docking molecule. Such chemical bonding may inactivate enzymes on the electrode surface through destabilization of the enzyme such as conformational changes of the enzyme body disrupting the function of the active site, denaturation of portions of the enzyme, or the like. As is shown in FIG. 1, an enzyme is either electrochemically active or electrochemically inactive depending either on the orientation of its active site relative to the electrode or its viability following the immobilization procedure. The active sites of enzymes that are viable and are oriented directly toward the electrode are shown hatched, indicating that they are electrochemically active enzymes. The active sites of enzymes that are not viable or are not oriented directly toward the electrode are shown unhatched, indicating that they are electrochemically inactive enzymes. FIG. 1 shows examples of electrochemically active enzymes, electrochemically inactive enzymes due to orientation, electrochemically inactive enzymes due to disrupted active sites, and electrochemically inactive enzymes due to destabilization. As such, attempts to orient enzymes toward the electrode through covalent docking and other techniques that may be disruptive to enzyme stability results in a limited number of electrochemically active enzymes at the electrode surface following immobilization.

Oxidoreductases makeup a class of enzymes that facilitate electron transfer reactions and play a critical role in virtually all metabolic pathways. As a result of their biological importance and use in bioelectrochemical devices, there has been a broad, sustained effort to develop strategies for interfacing such redox enzymes to an electrode surface. As outlined above, a primary challenge associated with such interfacing for creating enzyme electrodes having higher electrocatalytic activities is increasing the density of electrochemically active enzymes immobilized on the electrode surface.

According to Marcus theory, the terminal redox species of an electron transport chain needs to be within ~14 Å of the electrode to enable electron transfer at a rate that is fast relative to the enzymatic reaction. One prior approach that has been employed to minimize this distance involves the use of a unique docking motif to immobilize the protein in a desired orientation. As described above, however, such strategies are often accomplished at the cost of exceptionally high enzyme loading due to destabilization of the protein during the immobilization/orientation process. As another strategy, cross-linked polymers can be used to immobilize enzymes onto a variety of electrode surfaces and can stabilize such enzymes through electrostatic interactions; however, their tendency to form a large porous network disfavors the spatial positioning of protein near the electrode surface necessary for direct electron transfer (DET).

Figure 2:
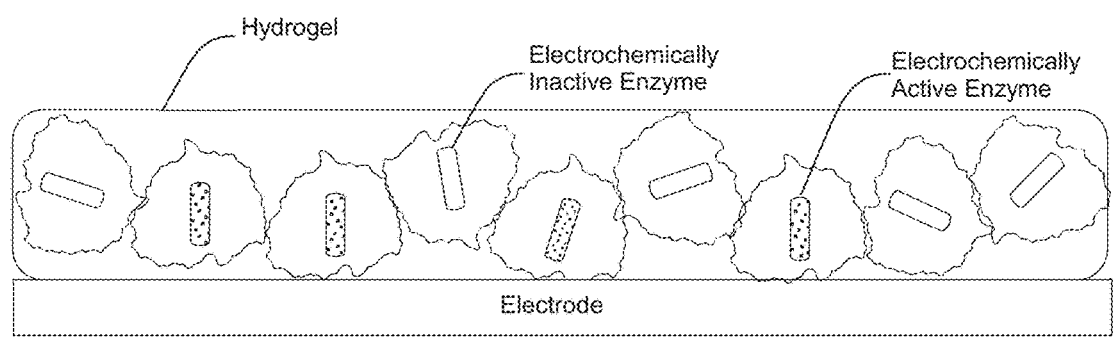
FIG. 2 illustrates an enzyme electrode in accordance with an example embodiment.

The present disclosure provides solutions to these problems by, among other things, focusing on preserving residual enzyme activity as opposed to enzyme orientation relative to an electrode surface. This is accomplished through the use of polymer materials designed to bind enzymes to an electrode surface in a manner that preserves a sufficient density of electrochemically active enzymes to enable efficient DET through random enzyme orientation alone. One benefit of this approach is that it does not require a specific enzymatic binding motif, which therefore enables a "plug and play" template for the use of a broad range of enzymes. FIG. 2 shows a very general illustration of such a binding motif of a hydrogel deposited on a surface of an electrode. The active sites of enzymes that are viable and are oriented directly toward the electrode are shown hatched, indicating that they are electrochemically active enzymes. The active sites of enzymes that are not oriented directly toward the electrode are shown unhatched, indicating that they are electrochemically inactive enzymes. The enzymes are immobilized within the hydrogel at a much lower rate of enzyme destabilization, if at all. Even given the number of electrochemically inactive enzymes in the hydrogel due to enzyme orientation, the number of electrochemically active enzymes in the hydrogel having a proper DET orientation represents a significant increase over prior immobilization techniques due to the lower rate of, or absence of, electrochemically inactive enzymes due to destabilization. The hydrogel immobilizes the enzymes sufficiently close to the electrode such that a higher proportion remain electrochemically active, as is shown by the hatched active sites of the enzymes.

Figure 3:
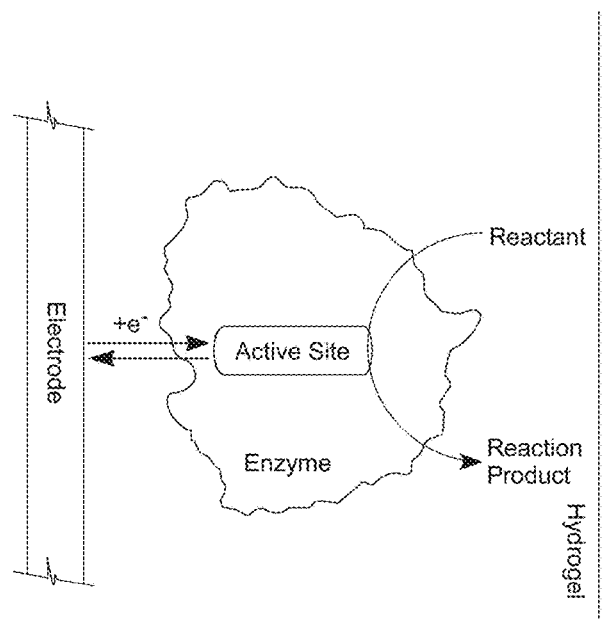
FIG. 3 illustrates direct electron transfer between an electrode and an enzyme in accordance with an example embodiment.

FIG. 3 shows one general example of an enzyme immobilized in a hydrogel (only the upper surface is shown, labeled "hydrogel") in proximity to an electrode. An electron transport pathway is shown between the electrode and the active site of the enzyme, which in this case, is catalyzing the reaction of a generic reactant into a generic reaction product.

As such, the nonlimiting examples and embodiments presented herein describe a broadly applicable approach for direct electrochemical communication with redox-active enzymes based on a water-permeable polymer that has been covalently modified with planar anchor moieties that function couple the water-permeable polymer to an electrode surface. The planar anchor-modified water-permeable polymer can be used to immobilize a wide variety of oxidoreductases by cross-linking the planar anchor-modified water-permeable polymer to form a bioelectric material, thus enabling direct bioelectrocatalysis. In some nonlimiting examples, the planar anchor-modified water-permeable polymer can be polymerized in the presence multiwalled carbon nanotubes (MWCNTs) at a carbon electrode.

In one example, the present disclosure provides an enzyme electrode. Such an enzyme electrode can be used for a variety of purposes, including biosensor applications, energy production, biocatalysis, electrosynthesis, and the like. For example, an enzyme electrode can function to catalyze a reaction to generate a reaction product from at least one reactant. In one specific example, an enzyme electrode can include an electrode having a bioelectric material electrically coupled thereto. In such a configuration, the bioelectric material provides an interface for the DET of electrons between the electrode and enzymes immobilized within the bioelectric material.

FIG. 4 illustrates one nonlimiting example of an enzyme electrode including an electrode 402 having a bioelectric material 404 disposed thereon. The bioelectric material 404 Includes a water-permeable polymer matrix 406 and a planar anchor 408. The planar anchor 408 couples the water-permeable matrix 406 to a surface of the electrode 402. In one example, the planar anchor 408 is covalently bonded to the water-permeable polymer matrix 406 and noncovalently bonded to the electrode 402. The planar anchor 408 is only shown in FIG. 4 at the interface between the electrode 402 and the water-permeable polymer matrix 406. It is understood, however, that other planar anchors may be present in the water-permeable polymer matrix 406 that are not shown for clarity of FIG. 4. Additionally, electrochemically active enzyme molecules (enzymes 410) are functionally embedded in the water-permeable polymer matrix 406. The active sites of enzymes 410 are positioned and oriented relative to the electrode 402 to allow DET between the active site and the electrode 402. FIG. 4 also shows a number of electrochemically inactive enzymes 412 that have active sites oriented away from the electrode 402.

The planar anchor can be any molecule having a planar terminus that can be covalently bonded to a water-permeable polymer and that is capable of stably coupling a matrix of the water-permeable polymer to an electrode surface via noncovalent bonding. Useful planar anchors can generally include a polycyclic aromatic hydrocarbon or a polycyclic highly conjugated hydrocarbon. Specific nonlimiting examples can include anthracene, benzofluorene, benzopyrene, chrysene, corannulene, coronene, ovalene, pentacene, phenalene, phenanthrene, porphyrin, pyrene, tetracene, triphenylene, and the like. More specific nonlimiting examples can include anthracene, porphyrin, and pyrene. One specific nonlimiting example of a useful planar anchor is pyrene, which is a polyaromatic hydrocarbon having four benzene rings in a planar configuration. FIG. 5A shows one example of pyrene covalently bonded to a generic polymer by a linker molecule. The linker molecule can be any molecule capable of covalently bonding pyrene to a polymer in a position that facilitates noncovalent bonding between an electrode surface and a sufficient number of pyrene molecules to adequately couple a water-permeable hydrogel thereto. In some nonlimiting examples, the linker molecule can be an amide, amine, ether, carbon-carbon, thiol, or ester linkage. One specific example of such a linkage, as shown in FIG. 5B, is created by reacting 1-pyrenebutyric acid N-hydroxysuccinimide ester with a polymer having an available nitrogen to produce a pyrene-modified polymer. FIG. 5C shows an example of such a reaction where 1-pyrenebutyric acid N-hydroxysuccinimide ester is reacted with linear poly (ethylenimine) (LPEI) polymer to produce pyrene-modified LPEI. The pyrene-modified LPEI can be used to form the water-permeable polymer component of a bioelectric material. In other examples, an LPEI polymer can be crosslinked to form the water-permeable polymer prior to modifying the LPEI with pyrene.

While "LPEI polymer" and "pyrene" are used throughout the present disclosure to describe water-permeable polymer and planar anchors, respectively, it is noted that this is for convenience in describing the present technology. These terms are not limiting, and any appropriate water-permeable polymer and planar anchor can be substituted in such description, unless the context clearly indicates otherwise.

Useful polymers for use as a water-permeable polymer can include any polymer species that can be functionalized with a planar anchor and crosslinked to form a hydrogel. Various polyamines, polyethers, polyamides, N-substituted polyamides, polyheterocycles, and the like, can be useful, provided they can be functionalized with a planar anchor and crosslinked to form a hydrogel. More specific nonlimiting examples can include polyethylenimine, polyvinyl alcohol, polyvinylamine, polyallylamine, polyvinylpyridine, polyvinylimidazole, and the like, including combinations thereof. In one specific example, the water-permeable polymer matrix comprises a polyethylenimine (PEI) polymer. In another example, the PEI polymer can be a linear PEI (LPEI) polymer. In other examples, PEI or LPEI can include a portion of branched PEI, provided the portion of branched PEI is not present in an amount that negatively affects the formation of the water-permeable matrix, the immobilization and function of the enzymes, or the like. Furthermore, in some examples, CNTs can be added to the polymer for incorporation into the water-permeable polymer matrix, which can increase catalytic current densities of the enzyme electrode. However, such an increase comes at the cost of increased capacitance. CNTs can be MWCNTs or single walled CNTs (SWCNTs).

The formation of hydrogels using various polymeric species is known in the art, and thus one of ordinary skill in the art would recognize specific conditions, such as a useful degree of crosslinking, needed for such hydrogel formation for a given polymeric species. The same would be true of the physical characteristics of the resulting hydrogels. Regardless, in one example, a water-permeable polymer matrix can include a polymer having a weight average molecular weight of from about 15-kD to about 1000-kD, measured using gel permeation chromatography. In another example, a water-permeable polymer matrix can include a polymer having a weight average molecular weight of from about 55-kD to about 100-kD, measured using gel permeation chromatography.

As described above, oxidoreductases can be useful enzymes to employ in an enzymatic electrode. Oxidoreductase enzymes are biocatalytic proteins that catalyze oxidation and reduction in two substrates, and thus function to transfer electrons between the two substrates. According to the present disclosure, one of the substrates is an electrode that can supply electrons to the active site of an enzyme (the second substrate) or that can receive electrons from the active site of an enzyme, depending on the configuration and function of a given enzyme electrode embodiment. While any useful oxidoreductase enzyme capable of activity while immobilized in a bioelectric material as described herein is considered to be within the present scope, specific nonlimiting examples can include nitrogenase, laccase, flavodoxin, ferredoxin, cytochrome c, hydrogenase, nitrate reductase, nitrite reductase, quinohemoproteins, multi-copper oxidases, heme containing enzymes, and the like, including combinations thereof. Nonlimiting examples of combinations of oxidoreductase enzymes used in combination can include various catalytic cascades, such as cytochromes P450, the heme-containing enzymes that catalyze C—H functionalization. In one specific example, the oxidoreductase enzyme includes nitrogenase. In another specific example, the oxidoreductase enzyme includes laccase. In yet another specific example, the oxidoreductase enzyme includes hydrogenase. In a further specific example, the oxidoreductase enzyme includes formate dehydrogenase. In an additional specific example, the combination of oxidoreductase enzymes includes multiple cytochromes P450.

Figure 6:
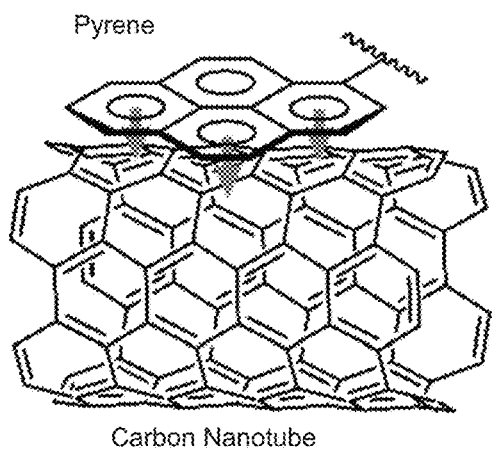
FIG. 6 illustrates noncovalent bonding between a pyrene anchor and a carbon nanotube surface in accordance with an example embodiment.

A variety of electrically conductive materials can be utilized in, or as, an electrode, and any such material is considered to be within the present scope provided the resulting electrode is capable of noncovalently binding to the planar anchors of the bioelectric material and electron transport/tunnel therebetween. Electrodes can be made from organic or inorganic materials, and can include carbon-based materials, semiconductors, metal oxides, conductive metal materials, and the like. In some cases, the electrode can be made from a carbon-based material such as, for example, CNTs, carbon infiltrated CNTs (CI-CNTs), SWCNTs, MWCNTs, graphene, carbon black, carbon felt, carbon powder, carbon fiber, carbon paper (Toray, ELAT, etc.), pyrolytic carbon, carbon cloth, screen printed carbon, doped diamond, doped diamond-like carbon (DLC), doped polycrystalline diamond (PCD), graphene-coated diamond, DLC, or PCD, and the like. For carbon-based electrode materials, a planar anchor such as pyrene can bind or otherwise adhere to a carbon surface through noncovalent pi-pi interactions. FIG. 6 shows one example of a pyrene anchor adhering to a CNT surface through such noncovalent bonding.

Electrodes can additionally be made from semiconductive materials, and any semiconductor material capable of electron transport/tunneling to and from the bioelectric material is considered to be within the present scope. Nonlimiting examples of semiconductor materials can include silicon, germanium, which can be doped with elements such as antimony, arsenic, boron, indium, gallium, phosphorus, or combinations thereof.

Electrodes made from conductive metals can also be used in the embodiments of the present disclosure. Any metal or metal alloy material that is electrically conductive, that can support a bioelectric material as described herein, and is capable of DET with enzymes immobilized in an adjacent hydrogel is considered to be within the present scope. Nonlimiting examples of such electrically conductive materials can include copper, gold, iron, platinum, nickel, silver, tungsten, and the like, including appropriate alloys and mixtures thereof.

Additionally, the present electrodes can be made from metal oxides, metal sulfides, and the like. Any oxide material that is electrically conductive, that can support a bioelectric material as described herein, and is capable of DET with enzymes immobilized in an adjacent hydrogel is considered to be within the present scope. Nonlimiting examples of oxides can include boron nitride materials, cerium oxide materials, indium-tin oxide (ITO), molybdenum sulfide, titanium oxides, including nanoporous titanium oxide, tin oxides, including tin oxide coated glass, and the like, including combinations thereof.

Figure 7:
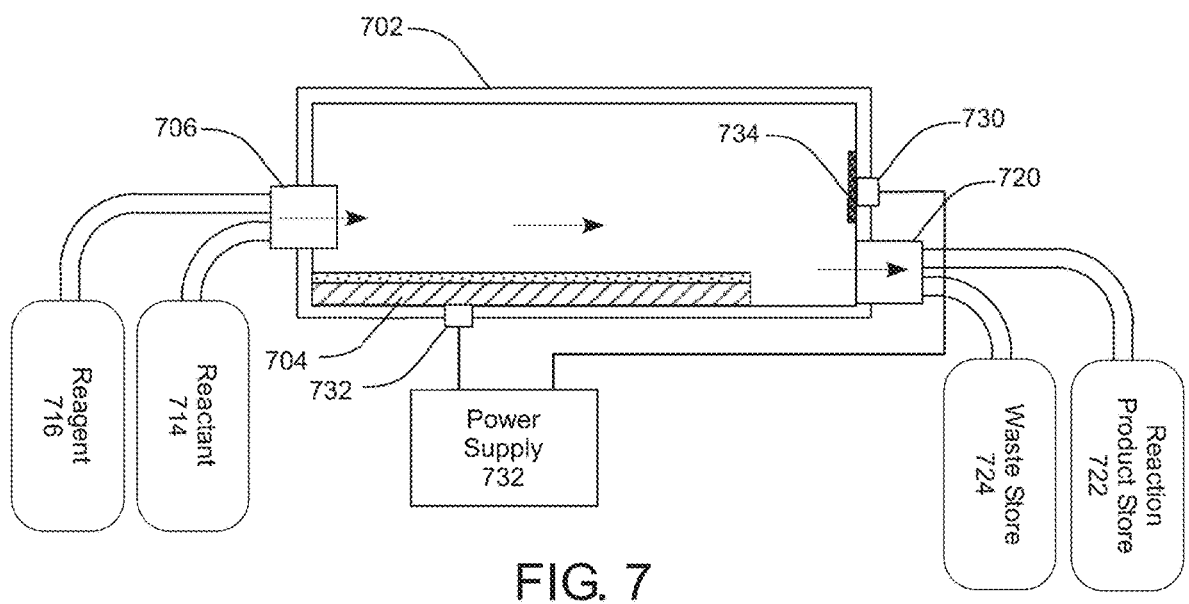
FIG. 7 illustrates a reaction chamber system in accordance with an example embodiment.

The present disclosure additionally provides systems that perform enzyme-mediated bioelectrocatalytic reactions on or across one or more enzyme electrodes. FIG. 7 shows one generalized example of such a system that includes a reaction chamber 702 and an enzyme electrode 704 positioned within the reaction chamber 702. The reaction chamber 702 further includes a reactant input 706 positioned to deliver a reactant from a reactant supply 714 to the enzyme electrode 704. FIG. 7 additionally shows a reagent supply 716 for delivering the reagent to the enzyme electrode 704, which can be through the reactant input 706 as shown or through a separate reagent input (not shown). The structure of the reaction chamber 702 is not limiting and has been simplified for clarity purposes. The arrow shown in FIG. 7 indicate the flow of reactant as it enters through the reactant input 706 and flows across the enzyme electrode 704. Depending on the design of the reaction chamber, the enzyme electrode can be oriented horizontally, vertically, or at a sloped angle therebetween. Furthermore, in some examples a liquid containing the reactant can flow across the enzyme electrode in a relatively thin liquid film. In other examples, the enzyme electrode can be submerged in the liquid containing the reactant. In an embodiment where the enzyme electrode is submerged, the liquid can be substantially still, such as for a reaction chamber where the liquid is introduced into the chamber prior to the reaction and removed from the reaction chamber following the reaction. In another embodiment where the enzyme electrode is submerged, the liquid can be flowed past the enzyme electrode, as a slow laminar flow, for example.

The reaction chamber 702 shown in FIG. 7 also includes a reaction product output 720, which is positioned in the reaction chamber 702 to receive a reaction product from the enzyme electrode, from which the reaction product is delivered to a reaction product store 722, where it can be collected for further processing. The reaction product output 720 can also retrieve waste products from the reaction chamber 702 and sent to a waste store 724. While the reaction product and waste are shown as being retrieved separately from the reaction chamber 702, such is not limiting. In other example embodiments, a total liquid product, or a partial liquid product, can be retrieved from the reaction chamber. The liquid product can be further processed to isolate the reaction product and, in some cases, retrieve reusable reagents and other components.

Additionally, the reaction chamber 702 can include power supply contacts 730 configured to electrically couple to a power supply 732 to provide electrical current to the enzyme electrode 704 and a counter electrode 734. The power supply 732 can be a separate from the reaction chamber 702 and removably couple to the power supply contacts during use. In other example embodiments, the power supply 732 can be coupled to, or integrated within, the reaction chamber 702.

Various reaction products can be generated by enzyme-mediated bioelectrocatalytic reactions within a reaction chamber. In one nonlimiting example, an enzyme electrode can include the oxidoreductase enzyme nitrogenase and the reaction chamber can be configured to generate ammonia as a reaction product. In another example, an enzyme electrode can include the oxidoreductase enzyme nitrogenase and the reaction chamber can be configured to generate methane as a reaction product. In yet another example, an enzyme electrode can include the oxidoreductase enzyme nitrogenase and the reaction chamber can be configured to generate ethylene as a reaction product. In a further example, an enzyme electrode can include the oxidoreductase enzyme nitrogenase and the reaction chamber can be configured to generate propylene as a reaction product. In yet another example, an enzyme electrode can include the oxidoreductase enzyme laccase and the reaction chamber can be configured to generate water as a reaction product.

Experimental Studies

Laccase Enzyme

Figure 8A:
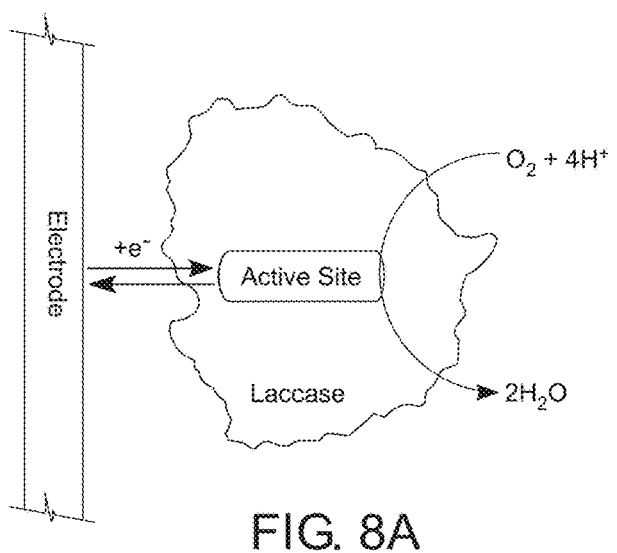
FIG. 8A illustrates direct electron transfer between an electrode and a laccase enzyme in accordance with an example embodiment.

Laccase is one example of an oxidoreductase enzyme that can be immobilized and stabilized in a cross-linked pyrene-modified hydrogel. Such an immobilized laccase enzyme can undergo DET for the electroenzymatic reduction of $O_2$. Laccase contains a single Cu atom near the protein surface (Cu—I) responsible for transferring electrons from an electron donor to a three-Cu cluster in the protein interior that catalyses the reduction of $O_2$ to water at 0.615±0.007 V vs SCE (see FIG. 8A). As such, direct bioelectrocatalysis of laccase depends on a sufficient quantity of the enzyme being oriented so the Cu—I site is within ~15 Å of the electrode surface.

Figures 8B, 8C:
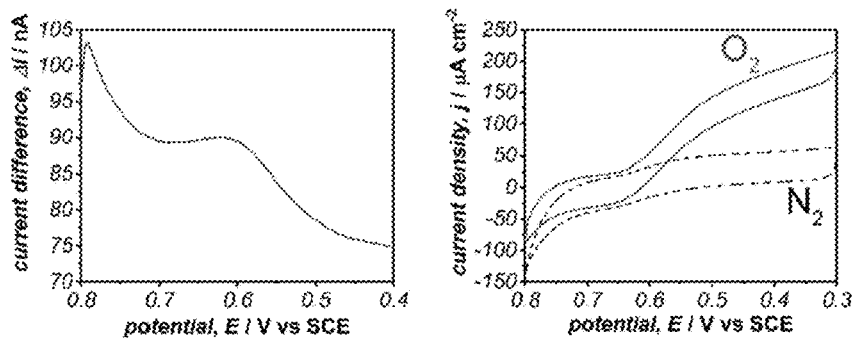
FIG. 8B illustrates square wave voltammogram data for the Cu—I site of laccase immobilized in a cross-linked pyrene-LPEI film in accordance with an example embodiment.
FIG. 8C illustrates cyclic voltammograms of a cross-linked pyrene-LPEI film under a bubbling of nitrogen or oxygen in accordance with an example embodiment.
Figure 8D:
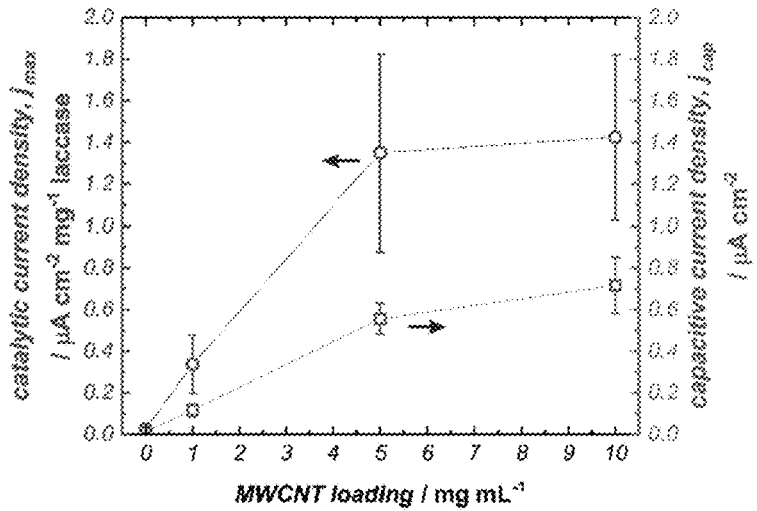
FIG. 8D illustrates a plot depicting the background-subtracted catalytic current density ($j_{max}$) and capacitive current density for pyrene-LPEI/laccase films in the presence of $O_2$ as a function of carbon nanotube loading in accordance with an example embodiment.

As one example, using LPEI as the water-permeable polymer, laccase/Pyrene-LPEI bioelectrode films were prepared by cross-linking pyrene-LPEI in the presence of laccase with ethyleneglycol diglycidyl ether (EGDGE) and coating the resulting solution onto 0.25 $cm^2$ Toray carbon paper electrodes so that each film contained 89 μg of enzyme per electrode with varying concentrations of MWCNTs. FIG. 8B shows square wave voltammogram data for the Cu—I site of laccase immobilized in a cross-linked pyrene-LPEI film and FIG. 8C shows cyclic voltammograms of the same cross-linked pyrene-LPEI film under a bubbling of nitrogen (- - -) or oxygen (—). The resulting films generated maximum catalytic current densities ($j_{max}$) of 40±10, 390±80, 1230±280, and 1880±80 μA $cm^{-2}$ $mg^{-1}$ laccase when containing 0, 1, 5 and 10 mg $mL^{-1}$ of carboxylated MWCNTs (MWCNT-COOH). As a point of comparison, a commonly employed method for bioelectrocatalytic reduction of $O_2$ by laccase utilizes anthracene-modified MWCNTs (An-MWCNTs) to orient the Cu—I centre towards the electrode surface and produces a limiting catalytic current density of 45 μA $cm^{-2}$ $mg^{-1}$ laccase. FIG. 8D shows a plot depicting the background-subtracted catalytic current density ($j_{max}$) (circles) and capacitive current density (squares) for pyrene-LPEI/laccase films in the presence of $O_2$ as a function of carbon nanotube loading. Cyclic voltammograms were performed using 100 mM citrate buffer at pH 4.5, 25° C. and a scan rate of 5 mV $sec^{-1}$.

A proposed cause for low catalytic current per enzyme observed in the previously published An-MWCNT docking method comes from decomposition of the enzyme during the electrode preparation process. Therefore, a spectroscopic assay was utilized in which 2,2'-azino-bis(3-ethylbenzothiazoline-6-sulphonic) acid (ABTS) is oxidized by laccase in the presence of $O_2$ to determine residual specific activity of the enzyme immobilized in pyrene-LPEI vs docked to An-MWCNTs in a film of tetrabutylammonium bromide modified Nafion© (TBAB/Nafion) film. For this assay, laccase was either immobilized onto the side of a cuvette with pyrene-LPEI or TBAB/Nafion with An-MWCNTs so that the films were submerged into assay solution but out of the beam path. By comparing the specific activity for each set of conditions with that of laccase dissolved in an aqueous solution, it was determined that for films of An-MWCNTs in TBAB/Nafion only 0.3±0.1% of laccase remained active, while 15±1% of laccase remained active in pyrene-LPEI films. This suggests that sufficient stabilization of the redox protein at the electrode surface may result in a statistical distribution of protein that is properly oriented through random chance.

It should be noted that, while the there is a clear correlation between $j_{max}$ and concentration of CNTs, this comes at the cost of increased capacitance that can obscure finer electroenzymatic features in a CV. Nevertheless, these results demonstrate that pyrene-LPEI films can immobilize a redox enzyme in the presence of CNTs to enhance bioelectrocatalytic turnover rates, but also suggest that the polymer may be used without CNT additives to study mechanistic features of more complex oxidoreductases.

MoFe-Dependent Nitrogenase Enzyme

Making up 78% of the Earth's atmosphere, $N_2$ is among the most abundant raw materials on the planet and is consequently an ideal substrate for the production of ammonia-based fertilizers. However, its gaseous nature and the exceptional strength of a N—N triple bond make $N_2$ a kinetic and thermodynamic sink, and as a result, the current process for converting $N_2$ to ammonia (the Haber-Bosch process) consumes>1% of global energy produced per year. A promising alternative to the Haber-Bosch process employs a Mo-dependent nitrogenase protein complex to catalyse the electrochemical reduction of $N_2$ to ammonia.

Specifically, Mo-dependent nitrogenase is part of a bi-enzyme cascade that includes a reducing protein (Fe protein) and a catalytic protein (MoFe). The MoFe protein contains a catalytic [7Fe-9S-Mo—C-homocitrate] (FeMoco) and a [8Fe-7S] cluster (P-cluster) that acts as an electron transfer bridge between the Fe protein and FeMoco. Mo-dependent nitrogenase is thought to operate by a redox-gated activation mechanism whereby the Fe protein binds transiently to the MoFe protein and where electron transfer is coupled to the hydrolysis of ATP to enable $N_2$ reduction at the FeMoco according to Equation I:

$$N_2 + 8H^+ + 8e^- + 16ATP \rightarrow 2NH_3 + H_2 + 16ADP + 16P_i \quad (I)$$

To achieve sustainable substrate reduction by nitrogenase without the need for ATP, there is considerable interest in delivering electrons directly to the MoFe protein. However, success can be commonly limited to $N_2H_4$, $H^+$, $NO_2^-$, HCN, and $N_3^-$ substrates at very low rates or by photochemical methods. We recently reported utilizing cobaltocene as a redox mediator to "wire" the P-cluster to an electrode surface and effectively regenerate the MoFe protein electrochemically. While this strategy was effective for electroenzymatically reducing $NO_2^-$ and $N_3^-$, the large overpotential of cobaltocene resulted in excessive electrochemical proton reduction to $H_2$, which acts as an inhibitor to the MoFe protein and consequently prevents the electrochemical reduction of $N_2$. Therefore, we hypothesized that pyrene-LPEI could be used to directly interface the P-cluster to minimize the required overpotential, limit electrochemical proton reduction and thereby enable electroenzymatic $N_2$ reduction using only the MoFe protein.

Figure 9A:
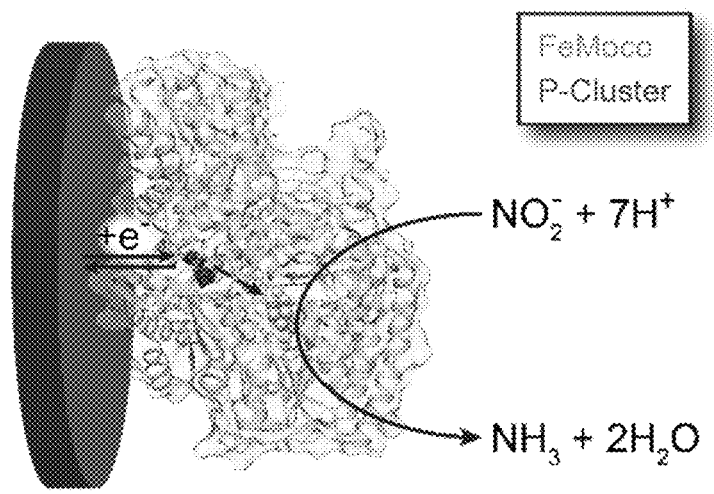
FIG. 9A illustrates direct electron transfer between an electrode and a MoFe enzyme in accordance with an example embodiment.
Figure 9B:
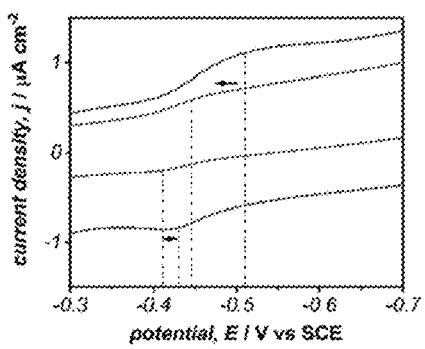
FIG. 9B illustrates a cyclic voltammogram for pyrene-LPEI films containing active or denatured MoFe protein in accordance with an example embodiment.
Figure 9C:
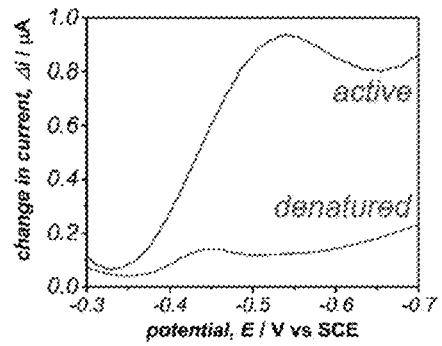
FIG. 9C illustrates a square wave voltammogram for pyrene-LPEI films containing active or denatured MoFe protein in accordance with an example embodiment.
Figure 9D:
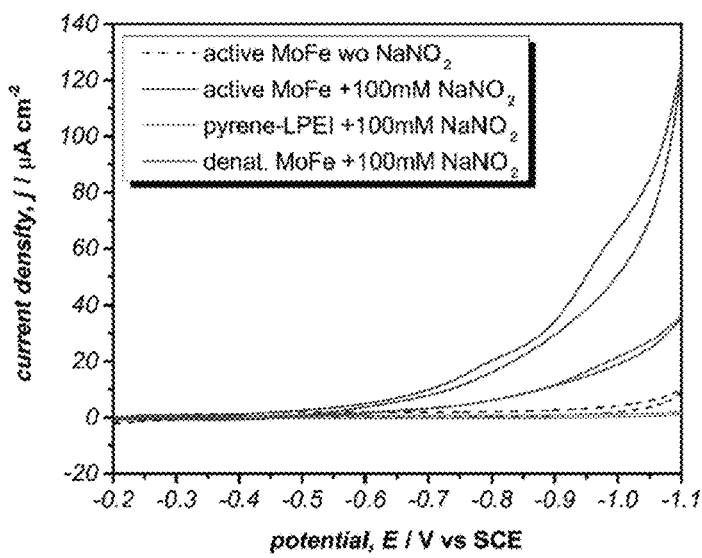
FIG. 9D illustrates a cyclic voltammogram of pyrene-LPEI films in containing active MoFe enzyme in the absence of nitrite or films containing active MoFe enzyme, denatured MoFe enzyme and without MoFe enzyme in the presence of 100 mM $NaNO_2$ in accordance with an example embodiment.

To test this, MoFe protein was immobilized in pyrene-LPEI onto Toray carbon paper electrodes using a procedure that was developed for laccase immobilization without MWCNTs. FIG. 9A shows an illustration depicting the proposed DET pathway for reduction of nitrite by MoFe protein. A combination of cyclic voltammetry and square wave voltammetry was used to identify a predominant redox feature at −0.51±0.01 V vs SCE. Based on previously suggested theoretical potentials, this peak was assigned to the P-cluster. As a control, the same experiment was performed with denatured MoFe, which resulted in shifted potential for the apparent P-cluster to −0.45±0.01 V vs SCE. FIG. 9B shows a cyclic voltammogram and FIG. 9C shows a square wave voltammogram for pyrene-LPEI films containing active (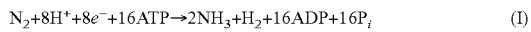) or denatured (~~~~) MoFe protein. This suggests that the reversible redox peak is evidence of direct electrochemical communication with the non-denatured MoFe protein. For further evidence of DET, we aimed to determine the ability of immobilized MoFe protein to exhibit direct bioelectrocatalysis. While $N_2$ is the native substrate for nitrogenase, its gaseous nature makes it difficult to utilize in activity assays and previous Fe protein-decoupled studies have employed $NO_2^-$ as a water-soluble nitrogenous substrate. Consequently, our initial electrochemical activity experiments for the MoFe protein were performed using aqueous $NaNO_2$. Cyclic voltammograms of the active MoFe protein immobilized in pyrene-LPEI exhibits a dramatically increased current density in the presence of 100 mM $NaNO_2$ when compared to either the denatured MoFe protein or the pyrene-LPEI film alone. FIG. 9D shows a cyclic voltammogram of pyrene-LPEI films in containing active MoFe in the absence of nitrite (- - -) or films containing active MoFe (——), denatured MoFe (~~~~) and without MoFe (~~~~) in the presence of 100 mM $NaNO_2$. CVs were performed using 100 mM MOPS buffer at pH 7.0, 25° C. and a scan rate of 5 mV sec$^{-1}$. It should be noted that the control employing denatured MoFe protein exhibits a small increase in current upon addition of $NO_2^-$; however, this is consistent with previous observations that the denatured P-cluster maintains residual activity towards nitrite. Nevertheless, these results suggest that the MoFe protein is both active inside the pyrene-LPEI film and is capable of direct bioelectrocatalysis.

Figure 10A:
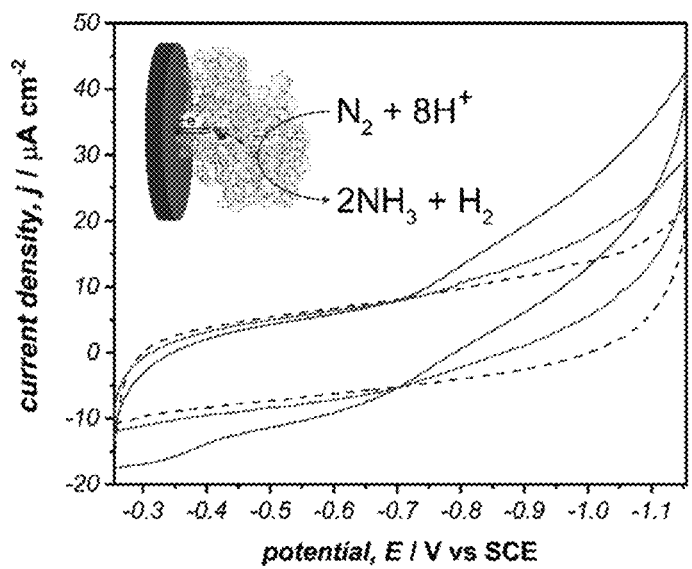
FIG. 10A illustrates cyclic voltammograms of pyrene-LPEI films containing MoFe protein and 5 mg mL$^{-1}$ MWCNT-COOH under Ar, and after 5 min, or 10 min of bubbling ultra-high purity $N_2$ in accordance with an example embodiment.
Figure 10B:
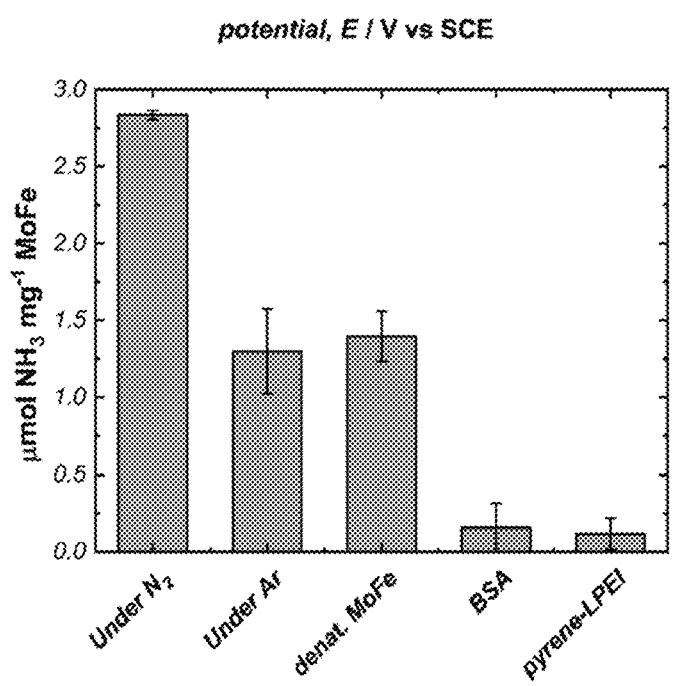
FIG. 10B illustrates production of $NH_3$ using $N_2$ as the only substrate after constant potential bulk electrolysis of pyrene-LPEI/MoFe films for 8 hrs in accordance with an example embodiment.

Next, we aimed to explore the ability of pyrene-LPEI/MoFe protein films to reduce $N_2$ via direct bioelectrocatalysis. Due to the high sensitivity of the in vitro MoFe protein to $O_2$, extreme care was taken to ensure that the electrochemical cell remained completely anaerobic. Bioelectrochemical activity of pyrene-LPEI/MoFe protein to $N_2$ was measured by cyclic voltammetry under Ar and increasing time of bubbling in ultra-high purity $N_2$. FIG. 10A shows cyclic voltammograms of pyrene-LPEI films containing MoFe protein and 5 mg mL$^{-1}$ MWCNT-COOH under Ar (- - -), and after 5 min (~~~~), or 10 min (——) of bubbling ultra-high purity $N_2$. The resulting voltammogram demonstrates an increasing current density with additional bubbling of $N_2$, which suggests that this is the first observation of bioelectrochemical $N_2$ in the absence of ATP. To confirm this result, we performed constant potential bulk electrolysis using electrodes coated with pyrene-LPEI containing active MoFe protein, denatured MoFe protein, BSA, and no protein in a sealed cell after bubbling ultra-high purity $N_2$ for 5 minutes. Products of the resulting electrolyses were analyzed by a fluorometric assay to confirm and quantify the production of $NH_3$. An aliquot of each electrolysis solution was combined with o-phthalaldehyde, which forms a fluorescent complex with $NH_3$. Product analysis demonstrated that the bioelectrosynthetic reduction of $N_2$ produced 247±3 nmol of $NH_3$ (2.83±0.03 μmol mg$^{-1}$ MoFe) compared to 10±9 nmol $NH_3$ for pyrene-LPEI without the MoFe protein. FIG. 10B shows production of $NH_3$ using $N_2$ as the only substrate after constant potential bulk electrolysis of pyrene-LPEI/MoFe films for 8 hrs. CVs were performed using 100 mM MOPS buffer at pH 7.0, 25° C. and a scan rate of 5 mV sec$^{-1}$. Bulk electrolysis was performed using 100 mM MOPS buffer pH 7.0 at −1.1 V vs SCE and 25° C. Error bars represent one standard deviation, where n=3.

Given the success of this method for studying direct bioelectrocatalysis of laccase and nitrogenase, we sought to investigate the extent of applicability to a small sample of additional redox proteins containing a relatively diverse set of electrochemical potentials and redox cofactors. The resulting pyrene-LPEI/protein combinations were studied by CV and SWV to confirm the electrochemical potential of each observed cofactor. The results are summarized in Table 1 and representative CVs are displayed in FIG. 11.

| Enzyme | Cofactor | pH | redox potential, E/V vs SCE | | |
|---|---|---|---|---|---|
| | | | This work | Literature | Ref. |
| laccase | Cu—I | 4.5 | 0.615 +/− 0.007 | 0.556 | 20 |
| cytochrome C | heme | 7.0 | −0.200 +/− 0.006 | −0.174 | 31 |
| MoFe protein (nitrogenase) | p-cluster [8Fe—7S] | 7.0 | −0.512 +/− 0.008 | −0.544 | 32 |
| ferrodoxin | [2Fe—2S] | 7.0 | −0.583 +/− 0.003 | −0.609 | 23 |
| flavodoxin | FMN | 7.0 | −0.727 +/− 0.008 | −0.688 | 33 |
| free FMN | FMN | 7.0 | −0.437 +/− 0.003 | −0.462 | 33 |

Table 1 shows a compilation of redox potentials obtained by square wave voltammetry of cross-linked pyrene-LPEI films containing 80 mg of protein per film. The same protein/hydrogel film preparation procedure was used for all proteins studied, and films were coated onto 0.25 cm$^2$ Toray electrode without the addition of CNTs.

Figure 11:
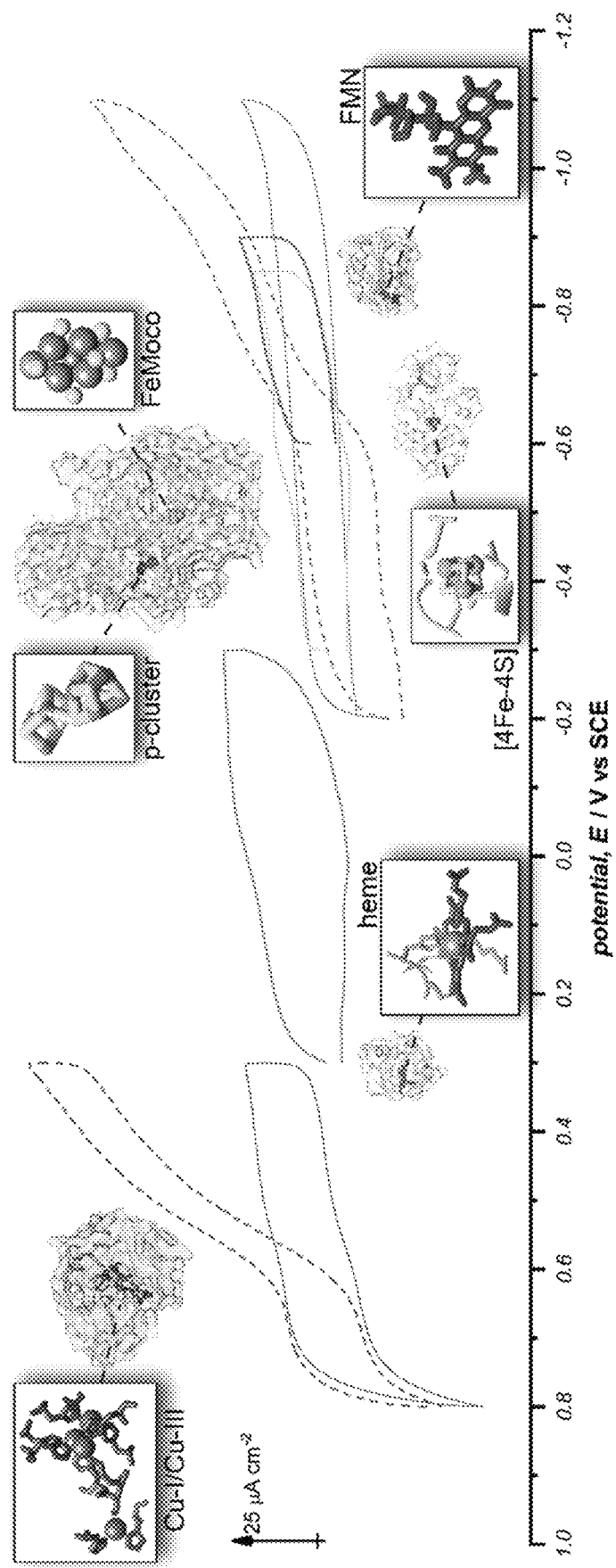
FIG. 11 illustrates cyclic voltammograms from a sample of redox proteins containing a relatively diverse set of electrochemical potentials and redox cofactors in accordance with an example embodiment.

FIG. 11 shows representative cyclic voltammograms of pyrene-LPEI films containing 5 mg mL$^{-1}$ MWCNT-COOH and laccase under nitrogen (━), laccase under O$_2$ (- - -), cytochrome C (·······), ferrodoxin (------), flavodoxin (∼∼∼), MoFe protein under argon (∼∼∼), and MoFe protein under N$_2$ (- - -) All pyrene-LPEI/protein films were prepared using a single procedure (ESI) without optimization for individual redox proteins. CVs were performed using 100 mM citrate (pH 4.5, for laccase), MOPS (pH 7.0 for MoFe protein), or phosphate (pH 7.0) at 25° C. and a scan rate of 5 mV sec$^{-1}$.

Results

It is thus reported a robust method based on a novel pyrene modified LPEI material for creating a direct bioelectrochemical interface between a series of redox proteins and a carbon electrode without the need for specific orientation. Using this method, we were able to demonstrate direct electron transfer to MoFe protein of the nitrogenase complex and subsequent direct bioelectrochemical synthesis of NH$_3$ from N$_2$ without the need for ATP nor an artificial redox mediator.

In one example, a pyrene-LPEI film/hydrogel is provided in which a redox enzyme, or a catalytic portion of a redox enzyme, is embedded via cross-linking, which is coated onto a carbon electrode. Depending on the specific enzyme and substrate, this composition can be used to generate ammonia and other materials.

In another nonlimiting example, enzymes that can be embedded in the pyrene-LPEI can include nitrogenase, laccase, flavodoxin, ferredoxin, horse cytochrome c, oxidoreductases, and the like, including any enzyme that catalyzes a reduction reaction. Reduction of O$_2$ to H$_2$O is provided using laccase as a catalyst, and reduction of N$_2$ to NH$_3$ is provided using the catalytic portion of nitrogenase (MoFe protein). The present technology can be applicable to any enzyme-driven chemical reduction process.

In one example, a material/method/process for utilizing an enzyme, nitrogenase, for the bioelectrochemical synthesis of ammonia from nitrogen gas and an aqueous proton source is provided. Using a newly developed polymer, pyrene-LPEI, we are able to immobilize the MoFe protein of nitrogenase onto a carbon electrode to facilitate the electroenzymatic reduction of nitrogen gas at −0.6 V vs SCE under neutral pH and ambient temperature. This polymer material stabilizes the MoFe protein to make it oxygen-tolerant, thereby enabling the bioelectrochemical production of ammonia under aerobic conditions.

As described herein, current industrial-scale ammonia production (the Haber-Bosch process) utilizes nitrogen and hydrogen gases from hydrocarbon feedstocks as starting materials and requires extreme temperature and pressure (500 C and 250 atm); consequently, it is estimated to be responsible for 2% of global energy consumption. Due to the centralized nature of the Haber-Bosch process, additional energy costs arise from transporting the resulting ammonia salts and solutions around the world. In one embodiment, the present disclosure enables the production of ammonia under ambient temperature, pressure and pH (25 C, 1 atm, pH 7.0), while using atmospheric nitrogen and protons from water as the feedstocks.

Enzymatic bioelectrocatalysis often requires an artificial redox mediator to observe significant electron transfer rates. The use of such mediators can add a substantial overpotential and obfuscate the protein's native kinetics, which limits the voltage of a biofuel cell and alters the analytical performance of biosensors, for example. Disclosed is a material for facilitating direct electrochemical communication with redox proteins based on a novel pyrene-modified linear poly(ethyleneimine). In one specific example, the material promotes direct bioelectrocatalytic reduction of O$_2$ by laccase and, by immobilizing the catalytic subunit of nitrogenase (MoFe protein), demonstrates the ATP-independent direct electroenzymatic reduction of N$_2$ to NH$_3$.

In another example, an enzymatic substrate is provided comprising an electrode, a LPEI material coupled to the electrode, and a redox enzyme or catalytic portion thereof cross-linked to the material, wherein upon activation of the electrode the enzymatic substrate generates an electroenzymatic reduction reaction.

EXAMPLES

Chemicals and Instruments

Purified laccase was purchased from Amano Enzyme Inc. Ethylene glycol diglycidyl ether (EGDGE) crosslinker was purchased from Polysciences, Inc; carboxylic acid functionalized multi-wall carbon nanotubes (MWCNT-COOH) were purchased from Cheap Tubes. All other chemicals used were purchased from Sigma Aldrich and used as received without further purification. Water used was filtered with Ultrapure MilliQ system. A gene of *Azotobacter vinelandii* encoding flavodoxin (nifF) and *Synechococcus* sp. encoding the [2Fe-2S] ferredoxin (petF) were purchased as a synthetic gene from Integrated DNA Technologies, Inc and a plasmid pBTR(hCc) was purchased from Addgene. A prelinearized pET28a expression vector (Novagen) from Gibson Assembly® and a QuikChange Lightning kit from Agilent Genomics were purchased. Primers were designed and produced by the DNA/peptide core facility at the University of Utah.

Pyrene-LPEI Synthesis

Referencing the reaction shown in FIG. 5C, Pyrene-LPEI was prepared by first dissolving 1-pyrenebutyric acid N-hydroxysuccinimide ester (pyrene-NHS, 0.269 g, 0.7 mmol) in a 1:1 DMSO/MeOH mixture (5 mL total volume) and then adding the pyrene-NHS solution into a stirring solution of linear poly(ethylenimine) (LPEI) (0.05 g, 1.2 mmol) in MeOH (5 mL). To ensure solubility throughout the reaction, $CH_2Cl_2$ (10 mL) was added to the reaction solution, which was then stirred for 24 hours at 35-40° C. in a closed flask to prevent evaporation. The reaction mixture was allowed to cool to room temperature, and MeOH and $CH_2Cl_2$ were evaporated under reduced pressure. The crude product mixture in DMSO was added dropwise to a stirring solution of toluene (150 mL), causing the polymer to precipitate rapidly. Toluene was decanted and the solid polymer was collected by vacuum filtration. The solid polymer was washed with THF (30 mL×3) to remove unreacted pyrene-NHS. Any remaining THF was evaporated under reduced pressure resulting in a pale yellow gel-like solid (0.18 g). The extent of LPEI substitution was determined by $^1$H-NMR ($CDCl_3$).

Figure 12A:
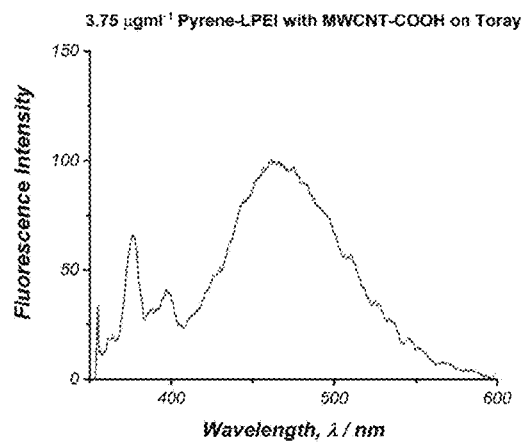
FIG. 12A illustrates a representative fluorescence of Pyrene-LPEI in accordance with an example embodiment.
Figure 12B:
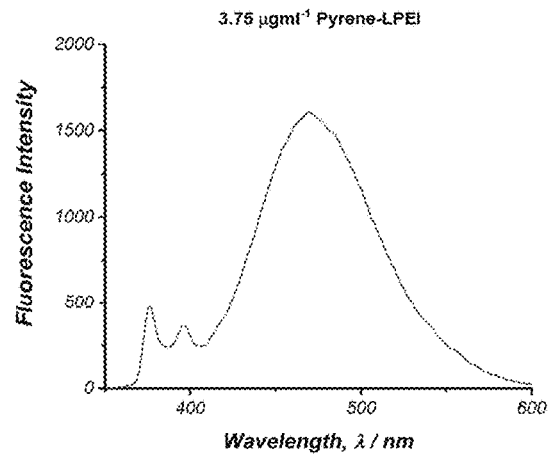
FIG. 12B illustrates representative fluorescence of Pyrene-LPEI with MWCNT-Toray carbon paper in a cuvette in accordance with an example embodiment.
Figure 12C:
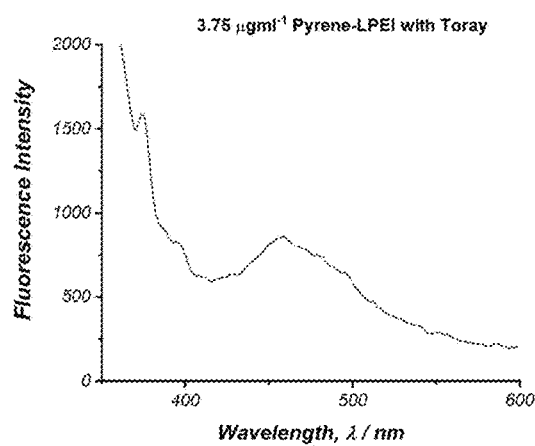
FIG. 12C illustrates representative fluorescence of Pyrene-LPEI with Toray carbon paper in a cuvette in accordance with an example embodiment.

The resulting polymer was determined by $^1$H-NMR to be substituted with pyrene pendant moieties on 22% of the backbone amines, and readily soluble in water up 10 mg $mL^{-1}$. Similar to pyrene, pyrene-LPEI exhibits two strong fluorescence bands at 475 and 375 nm that correspond to a self-pi-stacked excimer and 'free' pyrene, where the ratio of intensity for these peaks skews towards free pyrene at low concentrations (FIG. 12A). FIG. 12A shows a representative fluorescence of Pyrene-LPEI. A higher fluorescence intensity at 475 nm indicates a higher concentration of pyrene excimers than a non-complexed pyrene in the hydrogel solution. To determine the ability of pyrene-LPEI to pi-stack onto MWCNTs, a Toray carbon paper electrode coated in MWCNT-COOH was incubated in a fluorescence cuvette for 10 minutes. The resulting solution exhibited significant quenching of the excimer fluorescence band in the presence of both bare Toray carbon paper and MWCNT-coated Toray carbon paper, as is shown in FIGS. 12B and 12C. This is consistent with static quenching caused by the formation of pi-pi stacking complexes between pyrene and various carbon surfaces. FIG. 12B shows representative fluorescence of Pyrene-LPEI with MWCNT-Toray in a cuvette. The background fluorescence of MWCNT-Toray carbon paper in water was subtracted. FIG. 12C shows representative fluorescence of Pyrene-LPEI with Toray carbon paper in a cuvette. The background fluorescence of Toray carbon paper in water was subtracted.

Enzyme Expression and Purifications
Recombinant Horse Cytochrome c.

Purchased plasmid pBTR(hCc) was transferred into *E. coli* strain BL21(DE3) and was cultured by shaking at 37° C. in 5 mL rich medium overnight with ampicillin. This culture was used to inoculate 2 L of the same medium and was incubated while shaking at 37° C. for 30 hours. Cells were collected by 8000 rpm centrifugation.

The purification starts with adding 3 mL of lysis buffer per gram of cell collected and was stirred at room temperature for 1 hour and overnight at 4° C. This solution was pushed through a French press, then centrifugated for 20 minutes at 8000 rpm with an addition of ammonium sulphate to a final concentration of 300 g $L^{-1}$. After the centrifugation, the supernatant was dialyzed twice overnight in 10 L water and 2 L of low salt buffer, respectively. The dialysate was purified using S-Sepharose column via FPLC using a linear gradient of salt concentration. The purified cytochrome c was eluted at a high salt concentration.

Recombinant Flavodoxin (Fld)

Flavodoxin with a histidine tag (6×) at the C terminus was expressed in the nifF gene of *A. vinelandii*, which was cloned into a prelinearized pET28a expression vector. Mutant Cys69Ala flavodoxin protein (Fld) was generated using the QuikChange Lightning kit and primers were designed by the use of the associated software. Sequencing of the final plasmids confirmed the successful incorporation of the desired mutations. *E. coli* C43 cells were transformed with the corresponding vectors.

Mutant Fld was produced in *E. coli* C43 cells. A 20 mL starter was in Luria-Bertani (LB) medium at 37° C. at 200 rpm. This starter was used to culture 2 L of the same LB with 50 mg $L^{-1}$ kanamycin A. The cells were grown to the optical density at 600 nm ($OD_{600\ nm}$) of ~0.6-0.8 at 37° C. where protein expression was induced by the addition of isopropylthiogalactoside (IPTG) to a final concentration of 0.2 mM and flavin mononucleotide (FMN) to a final concentration of 10 mg $mL^{-1}$. After 12 h of induction shaken at 150 rpm at 30° C., the cells were harvested by centrifugation at 8000 rpm for 10 minutes, washed in 50 mM Tris, 200 mM NaCl buffer (pH 8). The collected cells were green with a final yield of 13 grams from a 2 L culture.

All purification steps were conducted anaerobically under an argon atmosphere. The cells were resuspended in Buffer A (50 mM Tris, 200 mM NaCl, 2 mM sodium dithionite (DT), 1 mM dithiothreitol (DTT) pH 8) with an addition of 50 μg DNAse and 1 mg $mL^{-1}$ lysozyme and the cell solution was left to react for 1 hour at 4° C. followed by sonication. The cell lysate was centrifuged at 26,000×g for 1 h at 4° C. Fld in the supernatant was purified by FPLC with immobilized metal affinity chromatography (IMAC) over HisTrap column (GE Healthcare, 5 mL) pre-equilibrated with buffer A, and then washed with buffer A containing 50 mM imidazole. Mutant Fld was eluted with buffer A containing 250 mM imidazole. In order to remove the imidazole, the eluted mutant Fld was loaded onto a HiPrep 26/10 desalting column pre-equilibrated with 50 mM Tris buffer pH 8.

Recombinant Ferredoxin

The growth and the purification of ferrodoxin was as follows: [2Fe-2S] ferredoxin (petF from *Synechococcus* sp.) was produced by *E. coli* C43 grown in LB medium containing 50 μs $mL^{-1}$ kanamycin A. The protein expression was induced once the $OD_{600}$ had reached ~0.6 by the addition of 0.2 mM IPTG and 50 μM $FeCl_3$. This cell culture was incubated for 6 hours at 30° C. and the cells were harvest in 50 mM MOPS, 300 mM NaCl buffer (pH 7) via centrifugation, washing and lysing the cells by the use of microfluidizer (3×passages @~18,000 psi). The collected cells were centrifuged again to collect the red supernatant that was purified with HiTrap columns (GE Healthcare, 5 mL) and HiPrep 26/10 desalting column pre-equilibrated with 50 mM MOPS buffer (pH 7). The final ferredoxin concentration was determined via the μ-bradford assay.

Nitrogenase

A mutant strain of *A. vinelandii* was grown and the N-terminal poly(histidine)-tagged MoFe that has been purified. Briefly, *A. vinelandii* was cultured in 18 L of Burk medium with 10 mM $NH_4^+$. Once the optical density of the culture was around 1.5 at 600 nm, the medium was switched to a $NH_4^+$ free Burk medium to encourage nitrogenase production.

Purification were performed in an anoxic tent ($O_2$<0.5 ppm). Cells were lysed via osmotic shock. His-tagged MoFe was purified by IMAC over HisTrap HP columns (GE Healthcare), before being purified further by anion exchange chromatography (Q-Sepharose, GE Healthcare) over a linear gradient of NaCl (200-650 mM). The final nitrogenase concentration was determined to be 27 mg $mL^{-1}$ via Biuret method.

Bioelectrode Fabrication
Preparation

Stock solutions of 10 mg mL$^{-1}$ enzyme (nitrogenase, laccase, flavodoxin, ferredoxin, and horse cytochrome c), 10 mg mL$^{-1}$ pyrene-LPEI, and 13 vol % ethyleneglycol diglycidyl ether (EGDGE, 6 µL in 45 µL H$_2$O) were prepared in water. Pyrene-LPEI/protein film coating solutions were prepared by first combining 70 µL of stock pyrene-LPEI solution with 30 µL of stock enzyme solution and vortexing briefly (~10 sec). To the pyrene-LPEI/protein solution was then added 3.75 µL of stock EGDGE solution, followed by additional vortexing (~10 sec). Pyrene-LPEI/protein/EGDGE solution (30 µL) was drop-coated onto a 0.25 cm$^2$ Toray electrode (0.5 cm×0.5 cm) in 10 µL increment, allowing 5-10 minutes to dry between each deposition. Modified electrodes were allowed to cure overnight and used without further purification. For films containing CNTs, the stock pyrene-LPEI solution was added to various amounts of carboxylated short multiwalled carbon nanotubes (MWCNT-COOH); this mixture was vortexed briefly (~30 sec) followed by the addition of protein and EGDGE solutions as described above.

Optimization of Pyrene-LPEI Hydrogel Using Laccase

Figure 13:
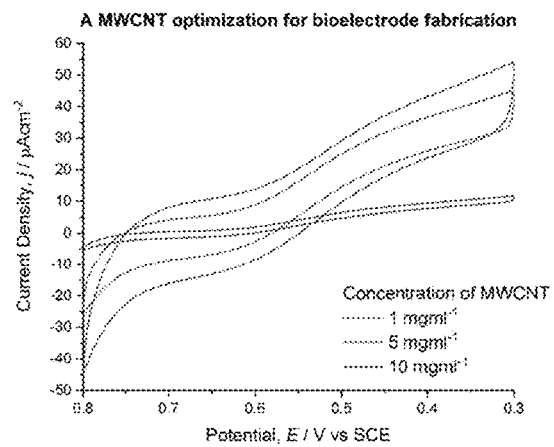
FIG. 13 illustrates cyclic voltammograms of different MWCNT concentrations using laccase solution in accordance with an example embodiment.

The bioelectrode solution was optimized using laccase by varying the final concentration of the EGDGE solution and the amount of MWCNT-COOH. The EGDGE solution was varied from 2.2 to 29% volume. The final bioelectrode solutions without MWCNT-COOH were deposited onto a glass surface and dried overnight. The deposited hydrogels were washed with water and any altercation to the shape of the hydrogel was monitored under UV-light. At 13% by volume or 6 µL of EGDGE in 39 µL of water showed the least shape change of the deposited hydrogels. The amount of MWCNT-COOH was varied to make a final concentration of 1 mg mL$^{-1}$, 5 mg mL$^{-1}$ and 10 mg mL$^{-1}$ solution. Any enhancement of electrochemical response was monitored by cyclic voltammetry. At 5 mg mL$^{-1}$ MWCNT-COOH, the electrochemical response was clearly observed without increasing the capacitance as shown in FIG. 13. FIG. 13 shows cyclic voltammograms of different MWCNT concentrations using laccase solution. O$_2$ gas was purged for 5 minutes prior to the experiment.

Electrochemical Experiments
Instruments and Techniques

All bioelectrodes made using nitrogenase, laccase, flavodoxin, and ferredoxin were tested using cyclic voltammetry (CV) with a scan rate of 5 mV sec$^{-1}$ and square-wave voltammetry (SWV) with a CH Instruments potentiostat. A three-electrode set up was used with a SCE reference electrode, a platinum mesh counter electrode, and Toray carbon paper electrodes.

Nitrogenase Bioelectrocatalysis

CVs of nitrogenase were performed in an inert atmosphere (Ar) glove box using 4 mL of a degassed 100 mM MOPS buffer of pH 7.0. As a substrate, a final concentration of 100 mM sodium nitrite was added. A three-electrode setup in a sealed round bottom glass was prepared with nitrogenase biocathode in 100 mM MOPS. N$_2$ (g) was bubbled into the apparatus between each CV performed.

Laccase Bioelectrocatalysis

CV of laccase was performed in air using 10 mL of 100 mM citric buffer of pH 4.5 from 0.8 V to 0.3 V at 5 mVs$^{-1}$. The buffer was bubbled with N$_2$ (g) for 5 minutes prior to performing the first CV. Afterwards, O$_2$ was bubbled for 5 minutes before the next CV was performed. A control CV was performed with bioelectrodes using C8-LPEI solution instead of Pyrene LPEI solution in the preparation step described in the chemicals and solution section herein.

Determination of Protein Redox Potentials

Square wave voltammetry (SWV) was performed for flavodoxin and ferredoxin electrodes. Then, a CV potential range was determined to be ±0.4 V from the SWV peak potentials.

Laccase Activity Assay Using ABTS
Laccase in Solution

A stock solutions of 0.54 mM ABTS (2,2'-azino-bis(3-ethylbenzthiazoline-6-sulphonic acid)), 0.1 mg mL$^{-1}$ laccase solution and 100 mM citric/phosphate buffer of pH 4.5 were prepared in water. All absorbance measurements were triplicated using Thermo 50 Scientific© Evolution 260 Bio UV-Visible Spectrophotometer.

Figure 14:
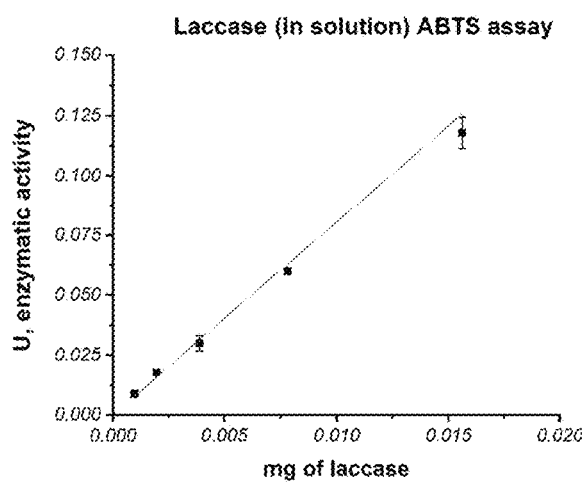
FIG. 14 illustrates a linear region of laccase activity in accordance with an example embodiment.

A stock solution of laccase was diluted to a range of concentrations in the buffer (0.063 mg mL$^{-1}$, 0.031 mg mL$^{-1}$, 0.016 mg mL$^{-1}$, 0.0078 mg mL$^{-1}$, 0.0039 mg mL$^{-1}$). 1.125 mL of 100 mM citric/phosphate buffer at pH 4.5, 0.125 mL of the ABTS stock solution, and 0.125 mL of a laccase solution at a desired concentration were added to a cuvette. The solution was mixed by inversions before monitoring the absorbance. FIG. 14 shows a linear region of laccase activity and the specific activity was calculated to be 8.1±0.3 U mg$^{-1}$ where U is defined as the amount of laccase that oxidized 1 µmol of ABTS per minute using the ABTS activity assay.

Laccase in Pyrene-LPEI Hydrogel

Figure 15:
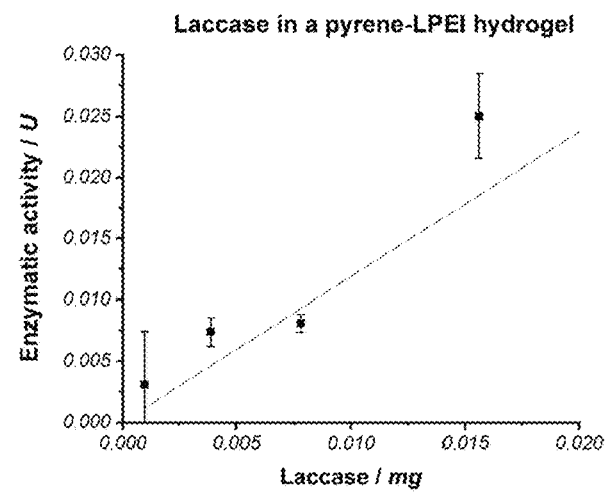
FIG. 15 illustrates a linear curve fitting of laccase activities in a pyrene-LPEI hydrogel in accordance with an example embodiment.

Using the same diluted laccase solution described above, bioelectrode solutions were prepared according to the chemicals and instruments section herein for electrochemical experiments without depositing onto Toray electrodes. Using 3 µL of this solution, a pyrene-LPEI hydrogel was deposited onto a cuvette avoiding the incident light but still in contact with the assay solution. The cuvettes were left to dry overnight before the absorbance was measured. FIG. 15 shows a linear curve fitting of laccase activities in a pyrene-LPEI hydrogel and the specific activity of a laccase in a pyrene-LPEI hydrogel is calculated to be 1.2±0.1 U mg$^{-1}$.

Laccase with Anthracene Modified Carbon Nanotubes

Figure 16:
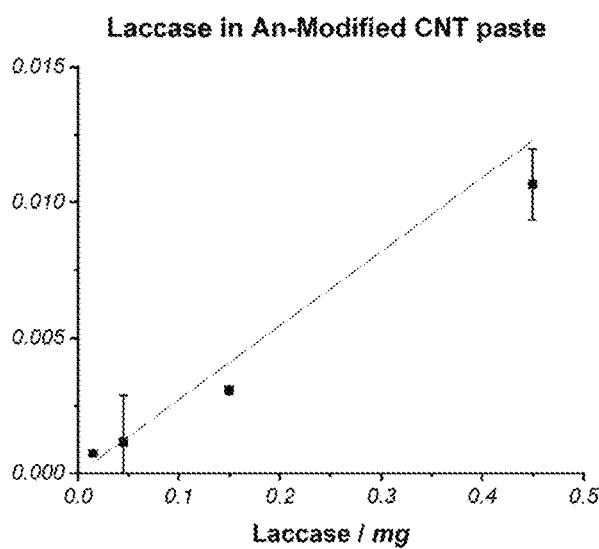
FIG. 16 illustrates a linear curve fitting of a laccase activity in An-CNT paste in accordance with an example embodiment.

A bioelectrode solution was prepared using 150 µL of the 100 mM citric/phosphate buffer, 3 mg laccase was dissolved and was mixed with 15 mg of anthracene modified carbon nanotubes (An-CNT). The mixture was sonicated for 10 minutes, briefly vortexed and 50 µL of TBAB-modified Nafion was lastly added. The final mixture was briefly vortexed and sonicated. Onto each cuvette, 1 µL, 3 µL, 10 µL, and 30 µL of the final mixture was deposited. For the ABTS activity assay, 0.318 mL of the stock ABTS solution and 3.182 mL of the 100 mM citrate/phosphate buffer was added to the cuvette prior to the experiment. A stir bar was placed in the cuvette for a uniform mixture through the experiment. FIG. 16 shows a linear curve fitting of a laccase activity in the An-CNT paste and the specific activity was calculated to be 0.027 U mg$^{-1}$.

Pyrene-LPEI Characterization
UV-VIS Characterization

Figure 17:
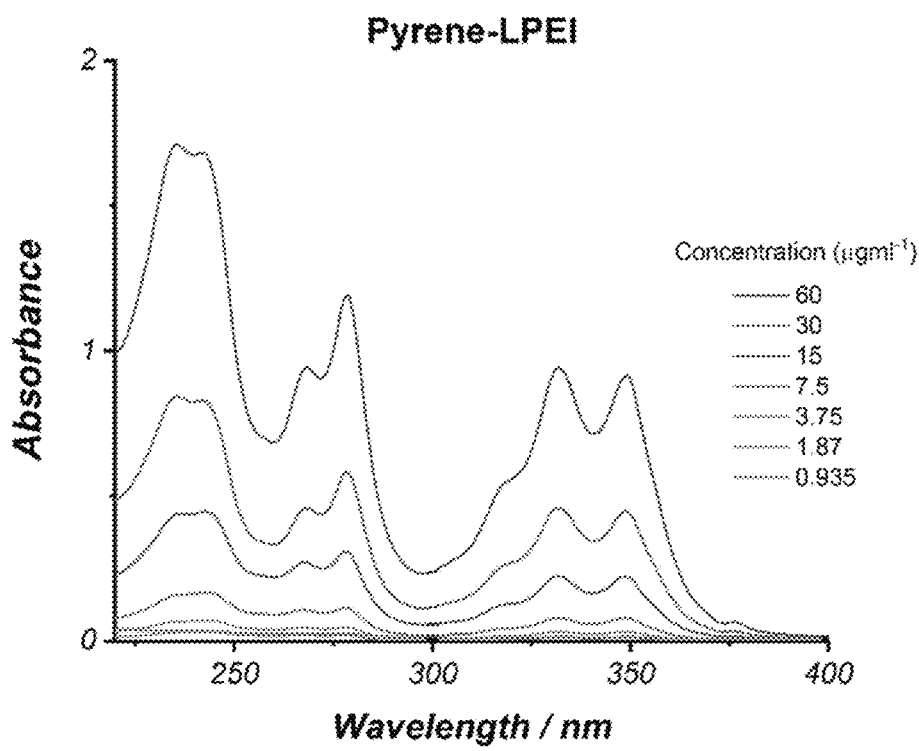
FIG. 17 illustrates a UV-visible full spectrum of pyrene-LPEI in accordance with an example embodiment.
Figure 18:
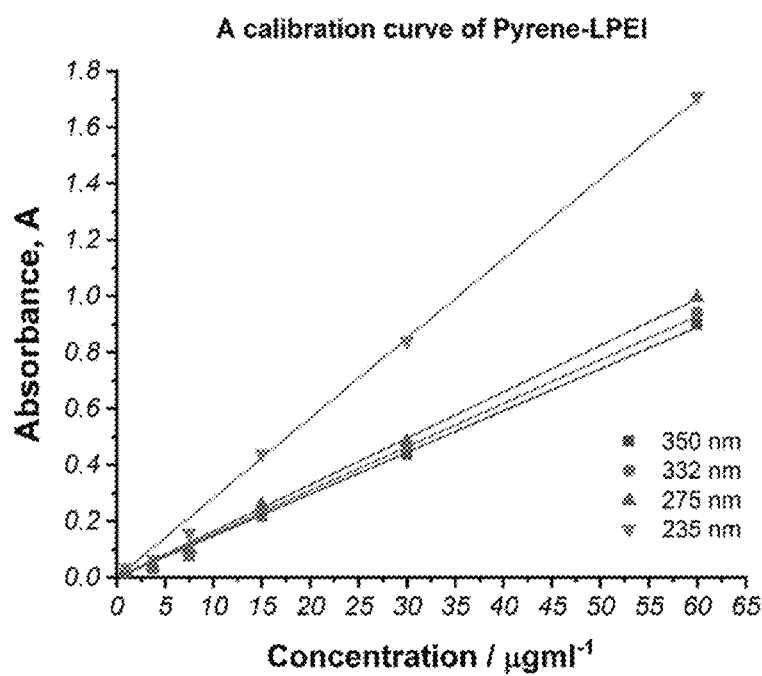
FIG. 18 illustrates a UV-visible spectrum calibration curve of pyrene-LPEI in accordance with an example embodiment.

A stock solution of pyrene LPEI was made by dissolving 2 mg of pyrene-LPEI in 5.04 mL of water. The stock solution was diluted to a concentration range from 60 µg mL$^{-1}$ to 0.94 µg mL$^{-1}$. Using UV-visible Spectrophotometer, the absorbance of each pyrene-LPEI solution was monitored from 220 nm to 600 nm. FIG. 17 shows a full spectrum of pyrene-LPEI. FIG. 18 shows a calibration curve of pyrene-LPEI and Table 2 shows the calculated molar absorptivity at each maximum wavelength.

TABLE 2

| | The calculated molar absorptivity of pyrene-LPEI | | |
|---|---|---|---|
| $\lambda_{max}$ | Molar absorptivity | error | R-squared |
| 350 nm | 0.0148 | 0.0003 | 0.99 |
| 332 nm | 0.0155 | 0.0003 | 0.99 |
| 275 nm | 0.0165 | 0.0002 | 0.99 |
| 235 nm | 0.0283 | 0.0004 | 0.99 |

Fluorescence Characterization

On a 3 cm long and 0.6 cm wide Toray paper, 300 µL of the MWCNT-COOH solution prepared by dispersing 5 mg of MWCNT in N-methyl-2-pyrrolidone (NMP) was deposited and dried completely prior to an experiment. A same sized Toray electrode was prepared without a MWCNT-COOH deposition. All florescence measurements were excited at 345 nm and the florescence intensity was monitored from 350 nm to 600 nm using the Hitachi Fluorescence Spectrophotometer F-7000. A quartz cuvette used in the experiment was cleaned using a pipe cleaner with water, ethanol and 1M sodium bicarbonate between each measurement.

A 3.75 µg mL$^{-1}$ pyrene-LPEI solution was used to measure the fluorescence intensity. A Toray paper was diagonally placed in a cuvette and the fluorescence intensity was measured. This step was repeated with the previously prepared MWCNT-Toray using a fresh 3.75 µg mL$^{-1}$ pyrene-LPEI solution. For a control experiment, water was used instead of the pyrene solution. At 375 nm, non-complexed pyrene was observed and at 475 nm, pyrene in an excimer formation (pi-stacked) was observed. At 390 nm, a scattering light is observed. Regardless of the placement of a Toray and MWCNT-Toray, excimer formation of pyrene-LPEI was observed as shown in FIGS. 12A-12C.

Figure 19A:
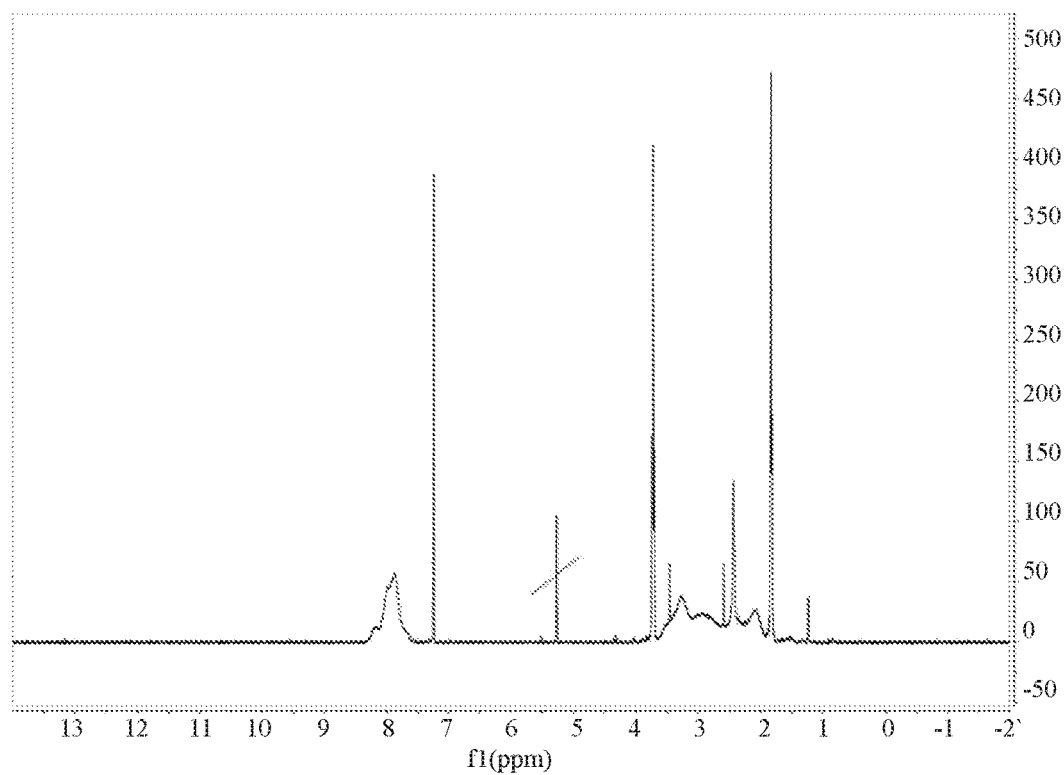
FIG. 19A illustrates the NMR spectra of Pyrene-LPEI in accordance with an example embodiment.
Figure 19B:
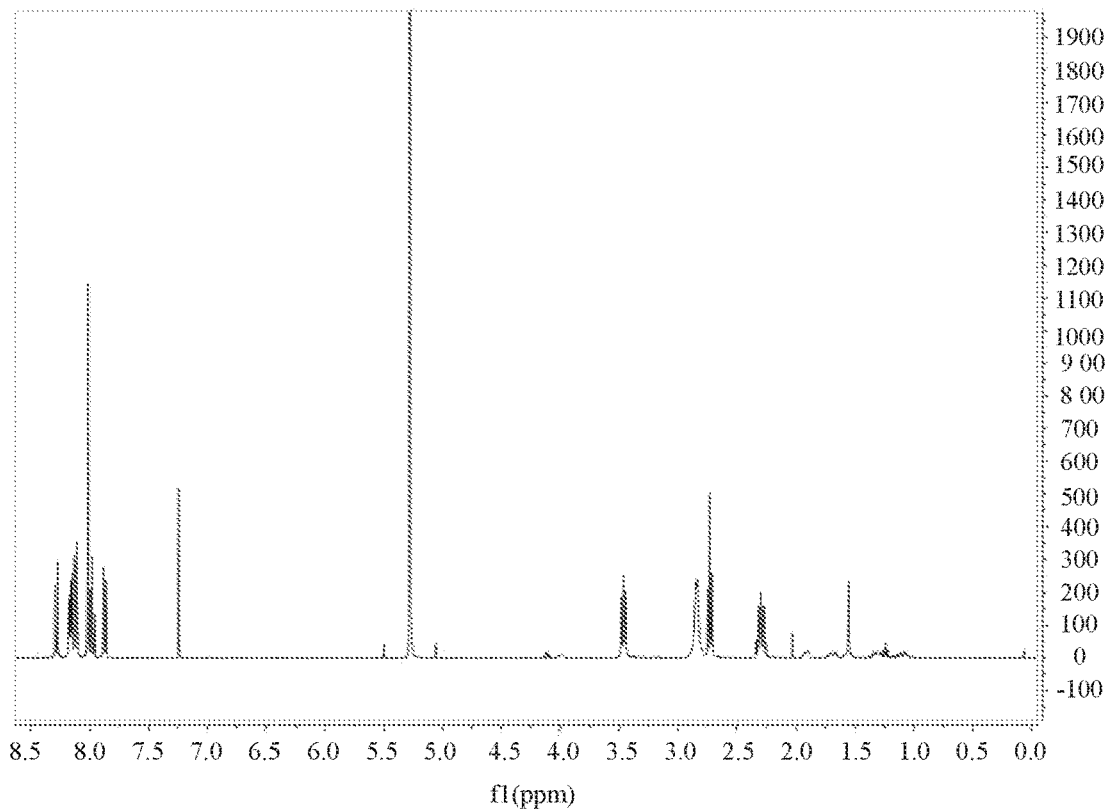
FIG. 19B illustrates the NMR spectra of 1-pyrenebutyric acid N-hydroxysuccinimide ester (pyrene-NHS) in accordance with an example embodiment.

$^1$H-NMR $^1$H-NMR was performed with the synthesized pyrene-LPEI in deuterated chloroform using 400 MHz NMR. The NMR spectra of Pyrene-LPEI and 1-pyrenebutyric acid N-hydroxysuccinimide ester (pyrene-NHS) are shown in FIGS. 19A and 19B, respectively. Pyrene substitution was calculated to be 22% using the equation: Pyrene percent substitution=4/(backbone hydrogen integration −2)*100.

Example Embodiments

The following examples pertain to specific embodiments and point out specific features, elements, or steps that can be used or otherwise combined in achieving such embodiments.

In one example, there is provided an enzyme electrode, comprising an electrode, a bioelectric material coupled to the electrode, the bioelectric material further comprising a water-permeable polymer matrix, a planar linker covalently coupled to the water-permeable polymer matrix and noncovalently coupled to the electrode, and electrochemically active oxidoreductase enzyme molecules functionally embedded in the water-permeable polymer matrix.

In one example of an enzyme electrode, the water-permeable polymer matrix comprises a covalently crosslinked hydrogel.

In one example of an enzyme electrode, the covalently crosslinked hydrogel comprises a polymer selected from the group consisting of polyamines, polyethers, polyamides, N-substituted polyamides, polyheterocycles, and mixtures and copolymers thereof.

In one example of an enzyme electrode, the covalently crosslinked hydrogel comprises a polymer selected from the group consisting of polyethylenimine, polyvinyl alcohol, polyvinylamine, polyallylamine, polyvinylpyridine, polyvinylimidazole, and mixtures and copolymers thereof.

In one example of an enzyme electrode, the water-permeable polymer matrix comprises a polyethylenimine (PEI) polymer.

In one example of an enzyme electrode, the PEI polymer is a linear PEI (LPEI) polymer.

In one example of an enzyme electrode, the planar linker is a polycyclic aromatic hydrocarbon or a polycyclic highly conjugated hydrocarbon.

In one example of an enzyme electrode, the planar linker includes a molecule selected from the group consisting of anthracene, porphyrin, and pyrene.

In one example of an enzyme electrode, the planar linker is pyrene.

In one example of an enzyme electrode, the water-permeable polymer matrix is comprised of a polymer having a weight average molecular weight of from about 55-kD to about 1000-kD.

In one example of an enzyme electrode, the water-permeable polymer matrix is comprised of a polymer having a weight average molecular weight of from about 55-kD to about 100-kD.

In one example of an enzyme electrode, the oxidoreductase enzyme molecules comprise an enzyme selected from the group consisting of nitrogenase, laccase, flavodoxin, ferredoxin, cytochrome c, hydrogenase, nitrate reductase, nitrite reductase, quinohemoproteins, multi-copper oxidases, heme containing enzymes, and combinations thereof.

In one example of an enzyme electrode, the oxidoreductase enzyme molecules comprise nitrogenase.

In one example of an enzyme electrode, the oxidoreductase enzyme molecules comprise nitrogenase, laccase, formate dehydrogenase, and hydrogenase.

In one example of an enzyme electrode, the electrode comprises a material selected from the group consisting of carbon nanotubes (CNTs), graphene, carbon black, carbon felt, indium-tin oxide (ITO), metals and metal alloys, and combinations thereof.

In one example of an enzyme electrode, the electrode comprises carbon nanotubes (CNTs).

In one example of an enzyme electrode, the CNTs further comprise infiltrated CNTs.

In one example of an enzyme electrode, the CNTs further comprise carbon infiltrated CNTs.

In one example of an enzyme electrode, the planar linker is a polycyclic aromatic hydrocarbon or a polycyclic highly conjugated hydrocarbon.

In one example of an enzyme electrode, the planar linker includes a molecule selected from the group consisting of anthracene, porphyrin, and pyrene.

In one example of an enzyme electrode, the planar linker is pyrene.

In one example, there is provided a system comprising a reaction chamber that further comprises an enzyme electrode positioned within the reaction chamber. The enzyme electrode comprises an electrode and a bioelectric material coupled to the electrode. The bioelectric material comprises a water-permeable polymer matrix, a planar linker covalently coupled to the water-permeable polymer matrix and noncovalently coupled to the electrode, and electrochemically active oxidoreductase enzyme molecules functionally embedded in the water-permeable polymer matrix. The reaction chamber further comprises a reactant input positioned to deliver a reactant to the enzyme electrode, a product output positioned to receive a reaction product from the enzyme electrode, and power supply contacts configured to electrically couple to a power supply and provide electrical current to the electrode when in use.

In one example of a system, the water-permeable polymer matrix comprises a covalently crosslinked hydrogel.

In one example of a system, the covalently crosslinked hydrogel comprises a polymer selected from the group consisting of polyamines, polyethers, polyamides, N-substituted polyamides, polyheterocycles, and mixtures and copolymers thereof.

In one example of a system, the covalently crosslinked hydrogel comprises a polymer selected from the group consisting of polyethylenimine, polyvinyl alcohol, polyvinylamine, polyallylamine, polyvinylpyridine, polyvinylimidazole, and mixtures and copolymers thereof.

In one example of a system, the water-permeable polymer matrix comprises a polyethylenimine (PEI) polymer.

In one example of a system, the PEI polymer is a linear PEI (LPEI) polymer.

In one example of a system, the planar linker is a polycyclic aromatic hydrocarbon or a polycyclic highly conjugated hydrocarbon.

In one example of a system, the planar linker includes a molecule selected from the group consisting of anthracene, porphyrin, and pyrene.

In one example of a system, the planar linker is pyrene.

In one example of a system, the water-permeable polymer matrix is comprised of a polymer having a weight average molecular weight of from about 55-kD to about 1000-kD.

In one example of a system, the water-permeable polymer matrix is comprised of a polymer having a weight average molecular weight of from about 55-kD to about 100-kD.

In one example of a system, the oxidoreductase enzyme molecules comprise an enzyme selected from the group consisting of nitrogenase, laccase, flavodoxin, ferredoxin, cytochrome c, hydrogenase, nitrate reductase, nitrite reductase, quinohemoproteins, multi-copper oxidases, heme containing enzymes, and combinations thereof.

In one example of a system, the oxidoreductase enzyme molecules comprise nitrogenase.

In one example of a system, the oxidoreductase enzyme molecules comprise nitrogenase, laccase, formate dehydrogenase, and hydrogenase.

In one example of a system, the electrode comprises a material selected from the group consisting of carbon nanotubes (CNTs), graphene, carbon black, carbon felt, indium-tin oxide (ITO), metals and metal alloys, and combinations thereof.

In one example of a system, the electrode comprises carbon nanotubes (CNTs).

In one example of a system, the CNTs further comprise infiltrated CNTs.

In one example of a system, the CNTs further comprise carbon infiltrated CNTs.

In one example of a system, the planar linker is a polycyclic aromatic hydrocarbon or a polycyclic highly conjugated hydrocarbon.

In one example of a system, the planar linker includes a molecule selected from the group consisting of anthracene, porphyrin, and pyrene.

In one example of a system, the planar linker is pyrene.

In one example of a system, the oxidoreductase enzyme molecules comprise nitrogenase and the reaction product is ammonia.

In one example of a system, the oxidoreductase enzyme molecules comprise laccase and the reaction product is water.

In one example of a system, the oxidoreductase enzyme molecules comprise nitrogenase and the reaction product is methane.

In one example of a system, the oxidoreductase enzyme molecules comprise nitrogenase and the reaction product is ethylene.

In one example of a system, the oxidoreductase enzyme molecules comprise nitrogenase and the reaction product is propylene.

In one example, there is provided a polymer substrate comprising a water-permeable polymer matrix and a planar linker covalently coupled to the water-permeable polymer matrix.

In one example of a polymer substrate, the water-permeable polymer matrix comprises a covalently crosslinked hydrogel.

In one example of a polymer substrate, the covalently crosslinked hydrogel comprises a polymer selected from the group consisting of polyamines, polyethers, polyamides, N-substituted polyamides, polyheterocycles, and mixtures and copolymers thereof.

In one example of a polymer substrate, the covalently crosslinked hydrogel comprises a polymer selected from the group consisting of polyethylenimine, polyvinyl alcohol, polyvinylamine, polyallylamine, polyvinylpyridine, polyvinylimidazole, and mixtures and copolymers thereof.

In one example of a polymer substrate, the water-permeable polymer matrix comprises a polyethylenimine (PEI) polymer.

In one example of a polymer substrate, the PEI polymer is a linear PEI (LPEI) polymer.

In one example of a polymer substrate, the planar linker is a polycyclic aromatic hydrocarbon or a polycyclic highly conjugated hydrocarbon.

In one example of a polymer substrate, the planar linker includes a molecule selected from the group consisting of anthracene, porphyrin, and pyrene.

In one example of a polymer substrate, the planar linker is pyrene.

In one example, a polymer substrate further comprises electrochemically active oxidoreductase enzyme molecules embedded in the water-permeable polymer matrix.

In one example of a polymer substrate, the oxidoreductase enzyme molecules comprise an enzyme selected from the group consisting of nitrogenase, laccase, flavodoxin, ferredoxin, cytochrome c, hydrogenase, nitrate reductase, nitrite reductase, quinohemoproteins, multi-copper oxidases, heme containing enzymes, and combinations thereof.

In one example of a polymer substrate, the oxidoreductase enzyme molecules comprise nitrogenase.

In one example of a polymer substrate, the oxidoreductase enzyme molecules comprise nitrogenase, laccase, formate dehydrogenase, and hydrogenase.

In one example of a polymer substrate, the planar linker is a polycyclic aromatic hydrocarbon or a polycyclic highly conjugated hydrocarbon.

In one example of a polymer substrate, the planar linker includes a molecule selected from the group consisting of anthracene, porphyrin, and pyrene.

In one example of a polymer substrate, the planar linker is pyrene.

In one example, there is provided a bioelectric material comprising a water-permeable polymer matrix, a pyrene linker covalently coupled to the water-permeable polymer matrix, and electrochemically active oxidoreductase enzyme molecules functionally embedded in the water-permeable polymer matrix.

In one example of a bioelectric material, the water-permeable polymer matrix comprises a covalently crosslinked hydrogel.

In one example of a bioelectric material, the covalently crosslinked hydrogel comprises a polymer selected from the group consisting of polyamines, polyethers, polyamides, N-substituted polyamides, polyheterocycles, and mixtures and copolymers thereof.

In one example of a bioelectric material, the covalently crosslinked hydrogel comprises a polymer selected from the group consisting of polyethylenimine, polyvinyl alcohol, polyvinylamine, polyallylamine, polyvinylpyridine, polyvinylimidazole, and mixtures and copolymers thereof.

In one example of a bioelectric material, the water-permeable polymer matrix comprises a polyethylenimine (PEI) polymer.

In one example of a bioelectric material, the PEI polymer is a linear PEI (LPEI) polymer.

In one example of a bioelectric material, the planar linker is a polycyclic aromatic hydrocarbon or a polycyclic highly conjugated hydrocarbon.

In one example of a bioelectric material, the planar linker includes a molecule selected from the group consisting of anthracene, porphyrin, and pyrene.

In one example of a bioelectric material, the planar linker is pyrene.

In one example of a bioelectric material, the oxidoreductase enzyme molecules comprise an enzyme selected from the group consisting of nitrogenase, laccase, flavodoxin, ferredoxin, cytochrome c, hydrogenase, nitrate reductase, nitrite reductase, quinohemoproteins, multi-copper oxidases, heme containing enzymes, and combinations thereof.

In one example of a bioelectric material, the oxidoreductase enzyme molecules comprise nitrogenase.

In one example of a bioelectric material, the oxidoreductase enzyme molecules comprise nitrogenase, laccase, formate dehydrogenase, and hydrogenase.

In one example of a bioelectric material, the planar linker is a polycyclic aromatic hydrocarbon or a polycyclic highly conjugated hydrocarbon.

In one example of a bioelectric material, the planar linker includes a molecule selected from the group consisting of anthracene, porphyrin, and pyrene.

In one example of a bioelectric material, the planar linker is pyrene.

In one example, there is provided a solution comprising a water-permeable polymer and a planar linker covalently coupled to the water-permeable polymer.

In one example of a solution, the water-permeable polymer comprises a polymer selected from the group consisting of polyamines, polyethers, polyamides, N-substituted polyamides, polyheterocycles, and mixtures and copolymers thereof.

In one example of a solution, the water-permeable polymer comprises a polymer selected from the group consisting of polyethylenimine, polyvinyl alcohol, polyvinylamine, polyallylamine, polyvinylpyridine, polyvinylimidazole, and mixtures and copolymers thereof.

In one example of a solution, the water-permeable polymer comprises a polyethylenimine (PEI) polymer.

In one example of a solution, the PEI polymer is a linear PEI (LPEI) polymer.

In one example of a solution, the planar linker is a polycyclic aromatic hydrocarbon or a polycyclic highly conjugated hydrocarbon.

In one example of a solution, the planar linker includes a molecule selected from the group consisting of anthracene, porphyrin, and pyrene.

In one example of a solution, the planar linker is pyrene.

In one example, a solution can further comprise electrochemically active oxidoreductase enzyme molecules.

In one example of a solution, the oxidoreductase enzyme molecules comprise an enzyme selected from the group consisting of nitrogenase, laccase, flavodoxin, ferredoxin, cytochrome c, hydrogenase, nitrate reductase, nitrite reductase, quinohemoproteins, multi-copper oxidases, heme containing enzymes, and combinations thereof.

In one example of a solution, the oxidoreductase enzyme molecules comprise nitrogenase.

In one example of a solution, the oxidoreductase enzyme molecules comprise nitrogenase, laccase, formate dehydrogenase, and hydrogenase.

In one example of a solution, the planar linker is a polycyclic aromatic hydrocarbon or a polycyclic highly conjugated hydrocarbon.

In one example of a solution, the planar linker includes a molecule selected from the group consisting of anthracene, porphyrin, and pyrene.

In one example of a solution, the planar linker is pyrene.

What is claimed is:

1. An enzyme electrode, comprising:
   an electrode;
   a bioelectric material coupled to the electrode, the bioelectric material further comprising:
   a water-permeable polymer matrix;
   a planar linker covalently coupled to the water-permeable polymer matrix and noncovalently coupled to the electrode; and
   electrochemically active oxidoreductase enzyme molecules functionally embedded in the water-permeable polymer matrix, wherein the water-permeable polymer matrix comprises a covalently crosslinked hydrogel.

2. The enzyme electrode of claim 1, wherein the covalently crosslinked hydrogel comprises a polymer selected from the group consisting of polyethylenimine, polyvinyl alcohol, polyvinylamine, polyallylamine, polyvinylpyridine, polyvinylimidazole, and mixtures and copolymers thereof.

3. The enzyme electrode of claim 1, wherein the water-permeable polymer matrix comprises a linear polyethylenimine (LPEI) polymer.

4. The enzyme electrode of claim 1, wherein the oxidoreductase enzyme molecules comprise an enzyme selected from the group consisting of nitrogenase, laccase, flavodoxin, ferredoxin, cytochrome c, hydrogenase, nitrate reductase, nitrite reductase, quinohemoproteins, multi-copper oxidases, heme containing enzymes, and combinations thereof.

5. The enzyme electrode of claim 1, wherein the oxidoreductase enzyme molecules comprise an enzyme selected from the group consisting of nitrogenase, laccase, formate dehydrogenase, hydrogenase, and combinations thereof.

6. The enzyme electrode of claim 1, wherein the electrode comprises a material selected from the group consisting of carbon nanotubes (CNTs), graphene, carbon black, carbon felt, indium-tin oxide (no), metals and metal alloys, and combinations thereof.

7. The enzyme electrode of claim 1, wherein the planar linker is a polycyclic aromatic hydrocarbon or a polycyclic highly conjugated hydrocarbon.

8. The enzyme electrode of claim 1, wherein the planar linker is pyrene.

9. A system, comprising:
a reaction chamber, comprising;
an enzyme electrode positioned within the reaction chamber, the enzyme electrode further comprising:
an electrode; and
a bioelectric material coupled to the electrode, the bioelectric material further comprising:
a water-permeable polymer matrix;
a planar linker covalently coupled to the water-permeable polymer matrix and noncovalently coupled to the electrode; and
electrochemically active oxidoreductase enzyme molecules functionally embedded in the water-permeable polymer matrix, wherein the water-permeable polymer matrix comprises a covalently crosslinked hydrogel;
a reactant input positioned to deliver a reactant to the enzyme electrode;
a product output positioned to receive a reaction product from the enzyme electrode; and
power supply contacts configured to electrically couple to a power supply and provide electrical current to the electrode when in use.

10. The system of claim 9, wherein the oxidoreductase enzyme molecules comprise an enzyme selected from the group consisting of nitrogenase, laccase, flavodoxin, ferredoxin, cytochrome c, hydrogenase, nitrate reductase, nitrite reductase, quinohemoproteins, multi-copper oxidases, heme containing enzymes, and combinations thereof.

11. The system of claim 9, wherein the oxidoreductase enzyme molecules comprise an enzyme selected from the group consisting of nitrogenase, laccase, formate dehydrogenase, hydrogenase, and combinations thereof.

12. The system of claim 9, wherein the oxidoreductase enzyme molecules comprise laccase and the reaction product is water.

13. The system of claim 9, wherein the oxidoreductase enzyme molecules comprise nitrogenase and the reaction product is a molecule selected from the group consisting of ammonia, methane, ethylene, propylene, and combinations thereof.

14. A polymer substrate, comprising:
a water-permeable polymer matrix; and
a planar linker covalently coupled to the water-permeable polymer matrix, wherein the planar linker is pyrene and the water-permeable polymer matrix comprises a covalently crosslinked hydrogel.

15. The polymer substrate of claim 14, wherein the covalently crosslinked hydrogel comprises a polymer selected from the group consisting of polyamines, polyethers, polyamides, N-substituted polyamides, polyheterocycles, and mixtures and copolymers thereof.

16. The polymer substrate of claim 14, wherein the covalently crosslinked hydrogel comprises a polymer selected from the group consisting of polyethylenimine, polyvinyl alcohol, polyvinylamine, polyallylamine, polyvinylpyridine, polyvinylimidazole, and mixtures and copolymers thereof.

17. The polymer substrate of claim 14, wherein the water-permeable polymer matrix comprises a linear polyethylenimine (LPEI) polymer.

18. The polymer substrate of claim 14, further comprising electrochemically active oxidoreductase enzyme molecules embedded in the water-permeable polymer matrix.

* * * * *